United States Patent [19]

Garland et al.

[11] 4,067,723
[45] Jan. 10, 1978

[54] PYRIDAZINE PESTICIDES

[75] Inventors: Ian Philip Garland, Angus, Scotland; Leslie Roy Hatton, Harold Wood, England; William George Leeds, London, England; Edgar William Parnell, Hornchurch, England

[73] Assignee: May & Baker Limited, Essex, England

[21] Appl. No.: 643,164

[22] Filed: Dec. 22, 1975

[30] Foreign Application Priority Data

Dec. 23, 1974 United Kingdom ............... 55473/74
Sept. 5, 1975 United Kingdom ............... 36743/75

[51] Int. Cl.² .................. C07D 237/08; A01N 9/22
[52] U.S. Cl. ................................. 71/92; 260/250 A;
260/347.8; 260/346.11; 260/347.2; 260/347.7;
260/347.3; 260/347.4

[58] Field of Search .................. 260/250 A; 71/92

[56] References Cited

U.S. PATENT DOCUMENTS 3,462,432   8/1969   Gall .................................. 260/250 A Primary Examiner—Paul M. Coughlan, Jr.
Assistant Examiner—Mark L. Berch Attorney, Agent, or Firm—Stevens, Davis, Miller & Mosher

[57] ABSTRACT

Pyridazine derivatives of the formula:

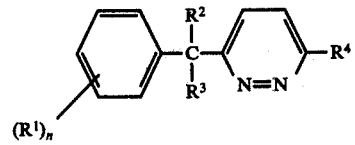

wherein $R^1$ represents a fluorine, chlorine, bromine or iodine atom or an alkyl, alkoxy, alkylthio, alkylsulphonyl, nitro, trifluoromethyl, cyano, alkoxycarbonyl, carboxy, aminocarbonyl, amino, monoalkylamino or dialkylamino group, $R^2$ represents a hydrogen atom or an alkyl group, $R^3$ represents a hydrogen, fluorine, chlorine or bromine atom or an alkyl, methoxy, ethoxy or hydroxy group, or $R^2$ and $R^3$ together represent an oxygen atom or a hydroxyimino group, $R^4$ represents a hydrogen atom or an alkyl group and $n$ represents zero or an integer from 1 to 5 inclusive, are new compounds useful as herbicides.

47 Claims, No Drawings

PYRIDAZINE PESTICIDES

This invention relates to new pyridazine derivatives, processes for their preparation, herbicidal compositions which contain them, and their use as herbicides.

According to the present invention, there are provided the new pyridazine derivatives of the general formula:

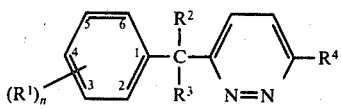

wherein $R^1$ represents a fluorine, chlorine, bromine or iodine atom or an alkyl, alkoxy, alkylthio, alkylsulphonyl, nitro, trifluoromethyl, cyano, alkoxycarbonyl, carboxy, aminocarbonyl, amino, monoalkylamino or dialkylamino group, $R^2$ represents a hydrogen atom or an alkyl group, $R^3$ represents a hydrogen, fluorine, chlorine or bromine atom or an alkyl, methoxy, ethoxy or hydroxy group, or $R^2$ and $R^3$ together represent an oxygen atom or a hydroxyimino (i.e. =NOH) group, $R^4$ represents a hydrogen atom or an alkyl group, and $n$ represents zero or an integer from 1 to 5 inclusive, and agriculturally-acceptable salts thereof, which compounds possess useful herbicidal activity. By the term 'agriculturally-acceptable salts' as used in the present specification is meant salts the anions and, when $R^1$ represents a carboxy group, the cations of which are known and accepted in the art for the formation of salts of herbicidally-active bases and, when $R^1$ represents a carboxy group, acids for agricultural or horticultural use, for example salts of inorganic acids, e.g. hydrochlorides, and, when $R^1$ represents a carboxy group, alkali metal, e.g. sodium or potassium, salts, alkaline earth metal, e.g. calcium or magnesium, salts and salts with strong organic bases, e.g. triethylamine, monoethanolamine, diethanolamine, triethanolamine and morpholine. It is to be understood that where reference is made in the present specification to the use of the compounds of general formula I as herbicides to control the growth of weeds, or to compositions containing them, such reference is intended to include also their agriculturally-acceptable salts. Alkyl groups represented by the symbols $R^1$, $R^2$, $R^3$ and $R^4$ and the alkyl moieties of alkoxy, alkylthio, alkylsulphonyl, alkoxycarbonyl, monoalkylamino and dialkylamino groups represented by the symbol $R^1$ may be straight- or branched-chain and contain from 1 to 6 carbon atoms. When $n$ represents an integer from 2 to 5 inclusive, the atoms and groups represented by the symbol $R^1$ may be the same or different. Atoms or groups represented by the symbol $R^1$ may be attached to any of the positions of the benzene ring.

As will be apparent to those skilled in the art, compounds depicted in general formula I may exist in isomeric forms. Compounds of general formula I wherein the atoms or groups represented by the symbols $R^2$ and $R^3$ are different may exist in optical, i.e. stereoisomeric, forms. Compounds of general formula I wherein $R^2$ and $R^3$ together represent a hydroxyimino group may exist in geometrically isomeric forms. The present invention comprises all isomeric forms of compounds depicted in general formula I and mixtures, including racemic mixtures, thereof.

Accordingly, a feature of the present invention is a method for controlling the growth of weeds (i.e. undesired vegetation) at a locus which comprises applying to the locus a herbicidally effective amount of at least one pyridazine derivative of general formula I. For this purpose, the pyridazine derivatives are normally used in the form of herbicidal compositions (i.e. in association with compatible diluents or carriers suitable for use in herbicidal compositions), for example as hereinafter described.

The compounds of general formula I show herbicidal activity against monocotyledonous (e.g. grass) and dicotyledonous (i.e. broad-leafed) weeds by pre- and post-emergence application. By the term 'pre-emergence application' is meant application to the soil in which the weed seeds or seedlings are present before emergence of the weeds above the surface of the soil. By the term 'post-emergence application' is meant application to the aerial or exposed portions of the weeds which have emerged above the surface of the soil. For example, the compounds of general formula I may be used to control the growth of annual grass weeds, such as wild oats (*Avena* spp., e.g. *Avena fatua*), blackgrass (*Alopecurus* spp., e.g. *Alopecurus myosuroides*), foxtails (*Setaria* spp., e.g. *Setaria viridis*), barnyard grass (*Echinochloa* spp., e.g. *Echinochloa crus-galli*), *Eleusine* spp., e.g. *Eleusine indica*, *Bromus* spp., crabgrass (*Digitaria* spp., e.g. *Digitaria sanguinalis*), ryegrass (*Lolium* spp., e.g. *Lolium perenne*), *Poa* spp., e.g. *Poa annua*, *Paspalum* spp., e.g. *Paspalum dilatatum*, silky bent (*Apera spica-venti*) and *Sorghum halepense*, and perennial grass weeds, e.g. *Agropyron repens*, *Agrostis* spp., e.g. *Agrostis stolonifera* and *Agrostis gigantea*, *Holcus mollis* and broad leaf species such as fat hen (*Chenopodium* spp., e.g. *Chenopodium album*), pigweeds (*Amaranthus* spp., e.g. *Amaranthus retroflexus*), *Polygonum* spp., (e.g. *Polygonum lapathifolium*, *Polygonum convolvulus* and *Polygonum aviculare*), chickweeds (*Stellaria* spp., e.g. *Stellaria media*), bedstraws [*Gallium* spp., e.g. cleavers (*Galium aparine*)], *Lamium* spp., mayweeds (*Matricaria* spp., e.g. *Matricaria inodora*), *Portulaca* spp., e.g. *Portulaca oleracea*, *Papaver rhoeas*, *Capsella bursa-pastoris*, *Sinapis* spp., e.g. *Sinapis arvensis*, *Thlaspi arvense*, and *Veronica* spp., e.g. *Veronica persica*, by pre-emergence and post-emergence applications. The compounds of general formula I also show herbicidal activity against aquatic weeds such as *Monochoria vaginalis* and *Rotala indica* and, particularly, sedges such as *Cyperus* spp., e.g. *Cyperus rotundus*, *Eliocharis* spp., e.g. *Eliocharis acicularis* and *Fimbristylis* spp. by pre- and post-emergence application and accordingly may be so-used to control the growth of those weeds.

The amounts of compounds of general formula I applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between ¼ and 8 kg., and more particularly between 1 and 4 kg., of active material per hectare give good results, particularly with the preferred compounds mentioned hereinafter, by pre-emergence application, and application rates between 1 kg. and 8 kg. of active material per hectare give good results, particularly with the preferred compounds mentioned hereinafter, by post-emergence application.

However, it must be understood that higher or lower application rates may be used, depending upon the particular problem of weed control encountered.

The compounds of general formula I may be used to control the growth of weeds by pre-emergence application, for example to control the growth of those species hereinbefore mentioned in connection with this mode of application, and to control the growth of weeds by post-emergence application, for example to control the growth of those species hereinbefore mentioned in connection with this mode of application, to a locus of weed infestation which may be an area used for growing crops, in particular beans, e.g. soyabeans, dwarf beans and tic beans, cotton, peas, flax (*linum usitatissimum*), sugar-beet, tomatoes, groundnuts, sunflowers, *Brassicas*, e.g. oil seed rape, cabbage, broccoli and Brussels sprouts, potatoes and cereals, e.g. barley, wheat, sorghum, maize, rye and rice, by application before or after the crop has emerged above the surface of the soil.

The compounds of general formula I are particularly suitable for use in the control of:

a. grass and broad-leafed weeds in crops of winter wheat, barley, rye, winter oil seed rape, *Brassicas*, winter beans, cotton, soyabeans, sugar-beet, peas, potatoes, tomatoes and maize, by application to the soil before weeds and crops emerge, more particularly (1) for the control of wild oats, blackgrass (e.g. *Alopecurus myosuroides*), silky bent (*Apera spica-venti*), annual meadow grass (*Poa annua*), ryegrass (e.g. *Lolium perenne*), chickweeds (e.g. *Stellaria media*), mayweeds (e.g. *Matricaria inodora*), *Veronica persica, Papaver rhoeas* and cleavers in winter wheat, barley, rye, winter oil seed rape, *Brassicas* and winter beans, and (2) for the control of crabgrass (e.g. *Digitaria sanguinalis*), barnyard grass (e.g. *Echinochloa crus-galli*), *Eleusine indica*, foxtails and pigweeds in cotton, soyabeans, dwarfbeans, sugar-beet, peas, potatoes, tomatoes and maize, b. grass and broad-leafed weeds in crops of maize, rice, sorghum, sugar-beet, cotton, beans, e.g. soyabeans, potatoes and tomatoes, by application to the soil before weeds emerge but after the crop emerges or is transplanted, more particularly (1) for the control of *Eleusine* spp., barnyard grass, crabgrass, foxtails and pigweeds in emerged crops of maize, rice, sorghum, sugar-beet, cotton and soyabean and (2) for the control of chickweed, mayweed, *Capsella bursa-pastoris*, wild oats and blackgrass in emerged crops of sugar-beet, *Brassicas*, beans, potatoes and tomatoes, c. grass and broad-leafed weeds in crops of winter wheat, winter oil seed rape and winter beans, by application to the foliage of seedling weeds before or after the crops emerge, more particularly for the control of wild oats, blackgrass (e.g. *Alopecurus myosuroides*), silky bent, annual meadow grass, ryegrass (e.g. *Lolium perenne*), chickweeds (e.g. *Stellaria media*), mayweeds (e.g. *Matricaria inodora*), *Veronica persica, Papaver rhoeas* and cleavers, and d. for use as a residual soil treatment to prevent competition from germinating seeds of the grasses hereinbefore mentioned and volunteer barley and wheat, and the broad-leafed weeds hereinbefore mentioned, in the crops hereinbefore mentioned from the time of application until the crop becomes well established, for example (1) to prevent the germination of seeds of *Eleusine* spp., crabgrass, barnyard grass and foxtails in emerged crops of maize, rice and sorghum and (2) to prevent the germination of seeds of chickweeds, wild oats, mayweeds and fathen in emerged crops of sugar-beet, oil seed rape, dwarf beans and potatoes.

The compounds of general formula I may be applied before sowing or planting of the crop, with, where necessary, incorporation in the soil in dry conditions, after sowing, but before emergence of the crop above the surface of the soil or after planting or emergence of the crop above the surface of the soil. The compounds of general formula I may also be used to control the growth of weeds by pre-emergence application to the soil or post-emergence to the foliage of the weeds in established, deep-rooted perennial crops, for example orchards, plantations, e.g. of rubber, oil palm and sugarcane, and shrubberies, including areas used for growing fruit-bearing bushes such as black currants and red currants, and ornamental shrubs and bushes. When used for such purposes in which a total herbicide effect is frequently desired, the active compounds may be applied at rates higher than those normally used to control the growth of weeds in areas used for growing crops as herein described. The precise dosage will depend upon the nature of the area treated and the effect sought.

Preferred compounds of general formula I for the control of weeds according to the present invention are those wherein $R^1$ represents a fluorine, chlorine, bromine or iodine atom or a methyl, ethyl, methoxy or ethoxy group, $R^4$ represents a hydrogen atom, $R^2$ and $R^3$ each represent a hydrogen atom, or $R^2$ represents a methyl or ethyl group and $R^3$ represents a hydrogen atom, or $R^2$ represents a hydrogen atom and $R^3$ represents a methoxy, ethoxy or hydroxy group, or $R^2$ and $R^3$ together represent an oxygen atom or a hydroxyimino group, and $n$ represents zero or an integer from 1 to 3 inclusive, and more particularly zero, 1 or 2, the substituent(s) represented by the symbol $R^1$ being preferably in the 2-, 2,3- or 2,4-position(s) of the phenyl group when $n$ represents 1 or 2.

Particularly preferred compounds of general formula I for the control of weeds are those wherein $R^1$ represents a fluorine, chlorine or bromine atom or a methyl, ethyl or methoxy group, $R^2$ represents a hydrogen atom and $R^3$ represents a hydroxy group or $R^2$ and $R^3$ together represent an oxygen atom, $R^4$ represents a hydrogen atom, $n$ represents 1 or 2 and the substituent(s) represented by the symbol $R^1$ are in the 2-, 2,3- or 2,4-position(s) of the phenyl group, $n$ preferably representing 1 and $R^1$ being a chlorine atom in the 2-position of the phenyl group, and especially those wherein $R^1$ represents a fluorine, chlorine or bromine atom or a methyl, ethyl or methoxy group, $R^2$ represents a hydrogen atom, $R^3$ represents an ethyl group, $R^4$ represents a hydrogen atom, $n$ represents 1 or 2 and the substituent(s) represented by the symbol $R^1$ are in the 2-, 2,3- or 2,4-position(s) of the phenyl group, and more especially those wherein $R^1$ represents a fluorine, chlorine or bromine atom or a methyl, ethyl or methoxy group, $R^2$ and $R^3$ each represent a hydrogen atom or $R^2$ represents a hydrogen atom and $R^3$ represents a methyl or methoxy group, $R^4$ represents a hydrogen atom, $n$ represents zero or, preferably, 1 or 2 and substituent(s) represented by the symbol $R^1$ are in the 2-, 2,3- or 2,4-position(s) of the phenyl group when $n$ represents 1 or 2, or $R^1$ represents a chlorine atom, $R^2$ represents a hydrogen atom, $R^3$ represents a methyl group, $R^4$ represents a hydrogen atom, n represents 1 and the chlorine atom represented by the symbol $R^1$ is in the 3-position of the phenyl group.

Individual compounds of particular value for the control of weeds are 3-(2-chloro-α-hydroxybenzyl)-pyridazine, 3-(2-chlorobenzoyl)pyridazine, 3-(2-methoxybenzoyl)pyridazine and 3-[1-(2-methylphenyl)-propyl]pyridazine, and, more especially, 3-(2-methylbenzyl)pyridazine, 3-(2-methoxybenzyl)pyridazine, 3-(2-chlorobenzyl)pyridazine, 3-(2-fluorobenzyl)pyridazine, 3-(2-bromobenzyl)pyridazine, 3-(2-ethylbenzyl)pyridazine, 3-(2-dimethylbenzyl)pyridazine, 3-(2,3-dimethylbenzyl)pyridazine, 3-(1-phenylethyl)pyridazine, 3-[1-(2-methylphenyl)ethyl]pyridazine, 3-[1-(2-chlorophenyl)ethyl]pyridazine, 3-[1-(2-fluorophenyl)ethyl]pyridazine, 3-[1-(2-bromophenyl)ethyl]pyridazine, 3-[1-(2-methoxyphenyl)ethyl]pyridazine, 3-[1-(2-ethylphenyl)ethyl]pyridazine, 3-[1-(2,4-dimethylphenyl)ethyl]pyridazine, 3-[1-(4-chloro-2-methylphenyl)ethyl]pyridazine, 3-[1-(2,3-dichlorophenyl)ethyl]pyridazine, 3-(2-methyl-α-methoxybenzyl)pyridazine, 3-(α2-dimethoxybenzyl)pyridazine, 3-(2-chloro-α-methoxybenzyl)pyridazine, 3-(2-bromo-α-methoxybenzyl)pyridazine, 3-(2-ethyl-α-methoxybenzyl)pyridazine and 3-[1-(3-chlorophenyl)ethyl]pyridazine.

According to a feature of the present invention, the compounds of general formula I wherein $R^1$, $R^4$ and $n$ are as hereinbefore defined, $R^2$ represents a hydrogen atom or an alkyl group and $R^3$ represents a hydrogen atom or an alkyl, methoxy, ethoxy or hydroxy group, i.e. the compounds of the general formula:

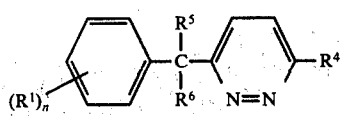

II (wherein $R^1$, $R^4$ and $n$ are as hereinbefore defined, $R^5$ represents a hydrogen atom or a straight- or branched-chain alkyl group containing from 1 to 6 carbon atoms, and $R^6$ represents a hydrogen atom or a straight- or branched-chain alkyl group containing from 1 to 6 carbon carbon atoms or a methoxy, ethoxy or hydroxy group), are prepared by reacting a compound of the general formula:

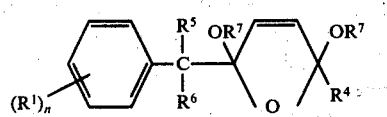

III (wherein $R^1$, $R^4$, $R^5$, $R^6$ and $n$ are as hereinbefore defined and $R^7$ represents a methyl or ethyl group) with an acid reagent capable of opening the furan ring, e.g. phenol or a dilute aqueous ethanolic solution of an inorganic acid, for example hydrochloric acid, followed by reaction of the compound formed with hydrazine.

The reactions may conveniently be effected by treating the compound of general formula III with a dilute aqueous ethanolic solution of an inorganic acid, e.g. hydrochloric acid, at between 20° and 100° C. followed by the addition of an excess of hydrazine hydrate or, as is preferred, by heating a mixture of the compound of general formula III, phenol and hydrazine hydrate at 120° C. under reflux.

According to a further feature of the present invention, the compounds of general formula I wherein $R^1$, $R^4$ and $n$ are as hereinbefore defined, $R^2$ represents a hydrogen atom or an alkyl group and $R^3$ represents a hydrogen atom, i.e. the compounds of the general formula:

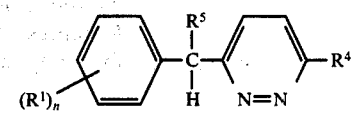

IV (wherein $R^1$, $R^4$, $R^5$ and $n$ are as hereinbefore defined), are prepared by reacting a compound of the general formula:

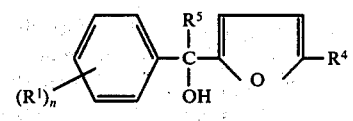

V (wherein $R^1$, $R^4$, $R^5$ and $n$ are as hereinbefore defined) with an acid reagent, for example an inorganic acid, e.g. aqueous hydrochloric acid or, preferably, an organic acid, e.g. a lower alkanoic acid, more particularly formic acid, and hydrazine. Hydrazine may conveniently be employed in the form of a salt, e.g. the dihydrochloride, or, preferably, in the form of its hydrate. The reaction may be effected in an inert organic solvent, for example a lower alkanol, e.g. methanol or ethanol, at an elevated temperature, e.g. at between 50° and 100° C., and conveniently at the reflux temperature of the reaction mixture.

According to a further feature of the present invention, the compounds of general formula I wherein $R^1$, $R^4$ and $n$ are as hereinbefore defined, $R^2$ respresents a hydrogen atom and $R^3$ represents a hydroxy group, i.e. the compounds of general formula:

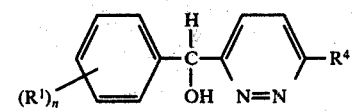

VI (wherein $R^1$, $R^4$ and $n$ are as hereinbefore defined), are prepared by reacting a compound of the general formula:

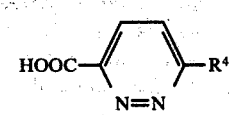

VII (wherein $R^4$ is as hereinbefore defined) with a compound of the general formula:

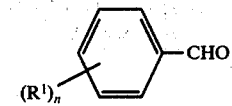

VIII (wherein $R^1$ and $n$ are as hereinbefore defined) by heating the compounds of general formulae VII and VIII together in an inert organic solvent, having a suitably high boiling point, e.g. between 100° and 200° C., for example an aromatic hydrocarbon, e.g. p-cymene, at a temperature at which carbon dioxide is freely evolved from the reaction mixture, e.g. at a temperature of from 120° to 160° C. and preferably at 140° C.

According to a further feature of the present invention, the compounds of general formula I wherein $R^1$, $R^4$ and $n$ are as hereinbefore defined, $R^2$ represents a hydrogen atom or an alkyl group and $R^3$ represents a fluorine, chlorine or bromine atom, i.e. the compounds of general formula:

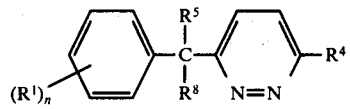

IX (wherein $R^1$, $R^4$, $R^5$ and $n$ are as hereinbefore defined and $R^8$ represents a fluorine, chlorine or bromine atom), are prepared from compounds of general formula VI, and corresponding compounds in which the depicted hydrogen atom in that formula is replaced by an alkyl group containing from 1 to 6 carbon atoms, by known methods for the conversion of a hydroxy group to a halogen atom, for example by treatment with a sulphur or phosphorus halide, for example thionyl chloride or phosphorus tribromide, at a temperature between 20° C. and the boiling temperature of the reaction mixture, optionally in the presence of an inert organic solvent, for example an aromatic hydrocarbon, e.g. benzene or toluene.

(By the term 'known methods' as used in the present specification is meant methods heretofore used or described in the chemical literature).

According to a further feature of the present invention, the compounds of general formula I wherein $R^1$, $R^4$ and $n$ are as hereinbefore defined and $R^2$ and $R^3$ together represent an oxygen atom, i.e. the compounds of general formula:

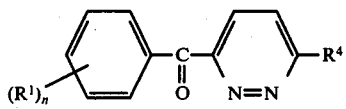

X (wherein $R^1$, $R^4$ and $n$ are as hereinbefore defined) are prepared from compounds of general formula VI (wherein $R^1$, $R^4$ and $n$ are as hereinbefore defined) by known methods for the oxidation of a secondary alcohol group to a carbonyl group, for example by treating a compound of general formula VI with chromium trioxide in dilute sulphuric acid at ambient temperature or, preferably, with potassium permanganate at a temperature of from 40° to 60° C.

According to a further feature of the present invention, the compounds of general formula I wherein $R^1$ and $n$ are as hereinbefore defined, $R^2$ represents a hydrogen atom or an alkyl group, $R^3$ represents a hydrogen atom or an alkyl group and $R^4$ represents a hydrogen atom, i.e. the compounds of general formula:

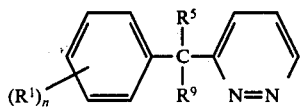

XI (wherein $R^1$, $R^5$ and $n$ are as hereinbefore defined and $R^9$ represents a hydrogen atom or a straight- or branched-chain alkyl group containing from 1 to 6 carbon atoms), are prepared by the reductive dehalogenation of a compound of the general formula:

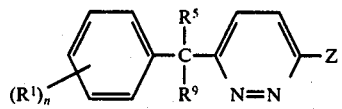

XII (wherein $R^1$, $R^5$, $R^9$ and $n$ are as hereinbefore defined and Z represents a chlorine or bromine atom) by known methods. Reduction is preferably carried out by hydrogenation with hydrogen under moderate pressure e.g. at a pressure from 1 to 10 atmospheres, and at a temperature of from 10° C. to 100° C. in the presence of a hydrogenation catalyst, e.g. palladium on charcoal, in the presence of a base, e.g. ammonium hydroxide or magnesium oxide, in an inert organic solvent, for example a lower alkanol, e.g. ethanol.

According to a further feature of the present invention, the compounds of general formula I wherein $R^1$, $R^4$ and $n$ are as hereinbefore defined, $R^2$ represents a hydrogen atom or an alkyl group and $R^3$ represents a hydrogen atom, i.e. compounds of general formula IV (wherein $R^1$, $R^4$, $R^5$ and $n$ are as hereinbefore defined), are prepared by the reductive dehalogenation of a compound of general formula IX (wherein $R^1$, $R^4$, $R^5$, $R^8$ and $n$ are as hereinbefore defined) by known methods, for example as hereinbefore described for the reductive dechlorination of compounds of general formula XII (wherein $R^1$, $R^5$, $R^9$ and $n$ are as hereinbefore defined) to compounds of general formula XI (wherein $R^1$, $R^5$, $R^9$ and $n$ are as hereinbefore defined).

Compounds of general formula III (wherein $R^1$, $R^4$, $R^5$, $R^6$, $R^7$ and $n$ are as hereinbefore defined) may be prepared by reacting a compound of the general formula:

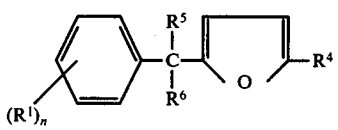

XIII (wherein $R^1$, $R^2$, $R^5$, $R^6$ and $n$ are as hereinbefore defined) with a halogen, e.g. chlorine, iodine or, preferably, bromine, in the presence of methanol or ethanol and a base, for example an alkali metal, preferably sodium, carbonate.

Compounds of general formula XIII wherein $R^1$, $R^5$ and $n$ are as hereinbefore defined, $R^4$ represents a hydrogen atom, and $R^6$ represents a hydrogen atom, a straight- or branched-chain alkyl group containing from 1 to 6 carbon atoms or a hydroxy group, i.e. compounds of the general formula:

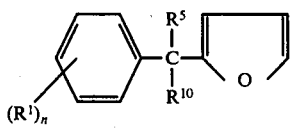

XIV (wherein $R^1$, $R^5$ and $n$ are as hereinbefore defined and $R^{10}$ represents a hydrogen atom, a straight- or branched-chain alkyl group containing from 1 to 6 carbon atoms or a hydroxy group), may be prepared by the decarboxylation of a compound of the general formula:

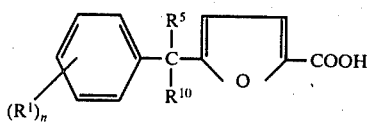  XV (wherein $R^1$, $R^5$, $R^{10}$ and $n$ are as hereinbefore defined) by heating with a decarboxylation catalyst, e.g. cupric oxide, at a temperature of from 150° to 230° C. optionally in the presence of an inert organic solvent of suitably high boiling point, e.g. quinoline.

Compounds of general formula XV (wherein $R^1$, $R^5$, $R^{10}$ and $n$ are as hereinbefore defined) may be prepared by the hydrolysis to a carboxy group of the ester group of a compound of the general formula:

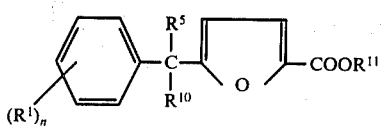  XVI wherein $R^1$, $R^5$, $R^{10}$ and $n$ are as hereinbefore defined, and $R^{11}$ represents an alkyl group containing from 1 to 4 carbon atoms. Preferably, hydrolysis is effected by treatment with an aqueous methanolic solution of an alkali metal, e.g. potassium, hydroxide at a temperature of from 20° to 100° C.

Compounds of general formula XVI (wherein $R^1$, $R^5$, $R^{10}$, $R^{11}$ and $n$ are as hereinbefore defined) may be prepared by reacting a compound of the general formula:

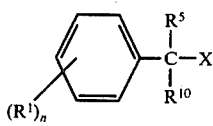  XVII (wherein $R^1$, $R^5$, $R^{10}$ and $n$ are as hereinbefore defined and X represents a halogen, preferably chlorine, atom) with a compound of the general formula:

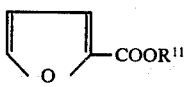  XVIII (wherein $R^{11}$ is as hereinbefore defined) in an inert organic solvent, e.g. carbon tetrachloride, and in the presence of a Friedel-Craft catalyst, for example aluminium trichloride, zinc chloride, stannic chloride, titanium tetrachloride, boron trifluoride or, preferably, ferric chloride, at a temperature between 0° and 100° C., preferably at the boiling temperature of the reaction mixture and more particularly at about 80° C.

Compounds of general formula XIII wherein $R^1$, $R^5$ and $n$ are as hereinbefore defined, $R^4$ represents an alkyl group and $R^6$ represents a hydrogen atom, a straight- or branched-chain alkyl group containing from 1 to 6 carbon atoms or a hydroxy group, i.e. compounds of the general formula:

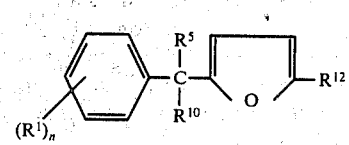  XIX (wherein $R^1$, $R^5$, $R^{10}$ and $n$ are as hereinbefore defined and $R^{12}$ represents a straight- or branched-chain alkyl group containing from 1 to 6 carbon atoms), may be prepared by the reduction of the carbonyl group of a compound of the general formula:

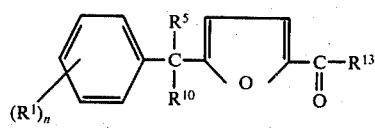  XX (wherein $R^1$, $R^5$, $R^{10}$ and $n$ are as hereinbefore defined and $R^{13}$ represents a hydrogen atom or a straight- or branched-chain alkyl group containing from 1 to 5 carbon atoms) by known methods for the reduction of a carbonyl group to methylene, for example by treatment with hydrazine hydrate and potassium hydroxide in ethylene glycol.

Compounds of general formula XX may be prepared from compounds of general formula XIV (wherein $R^1$, $R^5$, $R^{10}$ and $n$ are as hereinbefore defined) by known methods for the introduction of a carboxylic acyl group into a furan group, for example:

a. when $R^{13}$ represents an alkyl group, by reacting a compound of general formula XVII (wherein $R^1$, $R^5$, $R^{10}$, X and $n$ are as hereinbefore defined) with a compound of the general formula:

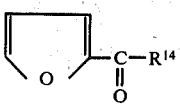  XXI (wherein $R^{14}$ represents a straight- or branched-chain alkyl group containing from 1 to 5 carbon atoms) in an inert organic solvent, e.g. carbon tetrachloride, and in the presence of a Friedel-Craft catalyst, for example aluminium trichloride, zinc chloride, stannic chloride, titanium tetrachloride, boron trifluoride or, preferably, ferric chloride, at a temperature between 0° and 100° C., preferably at the boiling temperature of the reaction mixture, and, more particularly, at about 80° C.;

b. when $R^{13}$ represents a hydrogen atom, by reacting a compound of general formula XIV with a mixture of phosphorus oxychloride and a disubstituted formamide derivative, e.g. dimethylformamide;

c. when $R^{13}$ represents an alkyl group, by reacting a compound of general formula XIV (wherein $R^1$, $R^5$, $R^{10}$ and $n$ are as hereinbefore defined) with an acid halide, e.g. acid chloride, or acid anhydride derived from a carboxylic acid of the general formula:

$R^{14}COOH$  XXII (wherein $R^{14}$ is as hereinbefore defined) in an inert organic solvent, e.g. carbon tetrachloride, in the presence of a Friedel-Craft catalyst, for example aluminium trichloride, zinc chloride, stannic chloride, titanium tetrachloride, boron trifluoride or, preferably, ferric chloride, at a temperature between 0° and 100° C., preferably at the boiling temperature of the reaction mixture, and, more particularly, at about 80° C.

Compounds of general formula XIII wherein $R^1$, $R^4$ and $n$ are as hereinbefore defined and $R^5$ and $R^6$ each represent a hydrogen atom, i.e. compounds of the general formula:

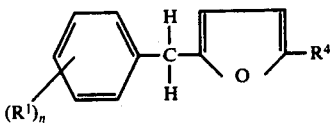
XXIII (wherein $R^1$, $R^4$ and $n$ are as hereinbefore defined), may be prepared by the reduction of a compound of the general formula:

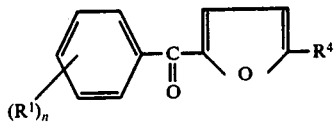
XXIV (wherein $R^1$, $R^4$ and $n$ are as hereinbefore defined) by heating with hydrazine hydrate in the presence of a base, for example sodium or, preferably, potassium hydroxide, in an alcoholic solvent, e.g. ethylene glycol, at a temperature of from 50° to 200° C. and preferably at a temperature of from 100° to 200° C.

Compounds of general formula XIII wherein $R^1$ and $n$ are as hereinbefore defined, $R^4$ represents a straight- or branched-chain alkyl group containing from 1 to 6 carbon atoms, and $R^5$ and $R^6$ each represent a hydrogen atom, i.e. compounds of the general formula:

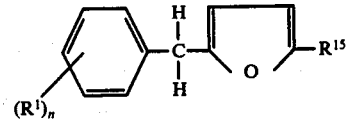
XXV (wherein $R^1$ and $n$ are as hereinabove defined and $R^{15}$ represents a straight- or branched-chain alkyl group containing from 1 to 6 carbon atoms), may be prepared by the reduction of a compound of the general formula:

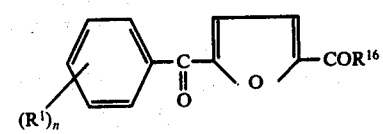
XXVI (wherein $R^1$ and $n$ are as hereinbefore defined and $R^{16}$ represents a hydrogen atom or a straight- or branched-chain alkyl group containing from 1 to 5 carbon atoms) by the procedures hereinbefore described for the reduction of compounds of general formula XXIV to give compounds of general formula XXIII.

Compounds of general formula XIII wherein $R^1$, $R^4$ and $n$ are as hereinbefore defined, $R^5$ represents a straight- or branched-chain alkyl group containing from 1 to 6 carbon atoms and $R^6$ represents a hydroxy group, i.e. compounds of the general formula:

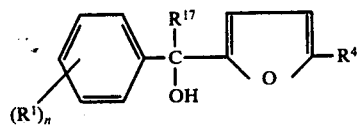
XXVII (wherein $R^1$, $R^4$ and $n$ are as hereinbefore defined and $R^{17}$ represents a straight- or branched-chain alkyl group containing from 1 to 6 carbon atoms), may be prepared by reacting a compound of general formula XXIV (wherein $R^1$, $R^4$ and $n$ are as hereinbefore defined) wih an organomagnesium halide of the general formula:

$R^{17}MgX$  XXVIII (wherein $R^{17}$ and X are as hereinbefore defined) or with an organolithium compound of the general formula:

$R^{17}Li$  XXIX (wherein $R^{17}$ is as hereinbefore defined) in an inert organic solvent, for example a lower alkyl ether, e.g. diethyl ether, at a temperature between 0° C. and the boiling temperature of the reaction mixture, and preferably at 5° to 15° C., and by hydrolysis of the organometallic compound thus obtained, for example by treatment with aqueous ammonium chloride solution.

Compounds of general formula XIII wherein $R^1$, $R^4$ and $n$ are as hereinbefore defined, $R^5$ represents a hydrogen atom and $R^6$ represents a hydroxy group, i.e. compounds of the general formula:

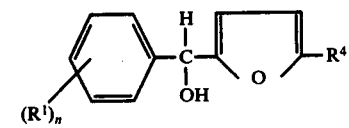
XXX (wherein $R^1$, $R^4$ and $n$ are as hereinbefore defined), may be prepared by the reduction of the carbonyl group of a compound of general formula XXIV (wherein $R^1$, $R^4$ and $n$ are as hereinbefore defined) by known methods for the reduction of a carbonyl group to an alcohol group, for example, by treatment with a borohydride, e.g. sodium borohydride, in an aqueous lower alkanol e.g. methanol, at a temperature of from 0° to 30° C. and preferably at a temperature of from 15° to 20° C.

Compounds of general fomula XXIV wherein $R^1$ and $n$ are as hereinbefore defined and $R^4$ represents a hydrogen atom, i.e. compounds of the general formula:

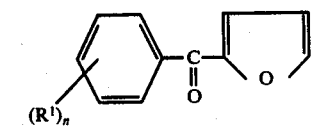
XXXI (wherein $R^1$ and $n$ are as hereinbefore defined), may be prepared by the decarboxylation of compounds of the general formula:

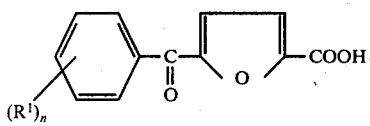
XXXII (wherein R¹ and n are as hereinbefore defined) by heating at a temperature at which carbon dioxide is evolved, e.g. 200° C., preferably in the presence of a decarboxylation catalyst, e.g. cupric oxide, and optionally in the presence of an inert organic solvent of suitably-high boiling point, e.g. quinoline.

Compounds of general formula XXXII (wherein R¹ and n are as hereinbefore defined) may be prepared by the hydrolysis of the ester group of a compound of the general formula:

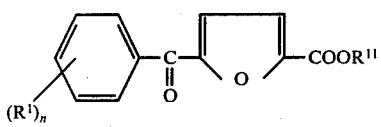
XXXIII (wherein R¹, R¹¹ and n are as hereinbefore defined) by treatment with a slight excess of an alkali metal, e.g. sodium or potassium, hydroxide in an aqueous lower alkanol, e.g. ethanol, at a temperature of from 20° to 100° C.

Compounds of general formula XXXIII (wherein R¹, R¹¹ and n are as hereinbefore defined) may be prepared by the condensation of an acid halide, e.g. an acid chloride or acid anhydride derived from an acid of the general formula:

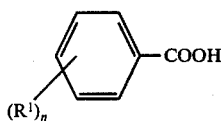
XXXIV (wherein R¹ and n are as hereinbefore defined) with a furoic ester of the general formula:

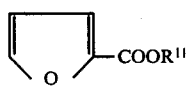
XXXV (wherein R¹¹ is as hereinbefore defined) in an inert organic solvent, e.g. carbon tetrachloride, in the presence of a Friedel-Craft catalyst, for example aluminium trichloride, zinc chloride, stannic chloride, titanium tetrachloride, boron trifluoride or, preferably, ferric chloride, at a temperature between 0° and 100° C., preferably at the boiling temperature of the reaction mixture and, more particularly, at about 80° C.

Compounds of general formula XXVI (wherein R¹ and n are as hereinbefore defined and R¹⁶ represents an alkyl group) may be prepared by the condensation of an acid halide, e.g. an acid chloride, or acid anhydride derived from an acid of general formula XXXIV (wherein R¹ and n are as hereinbefore defined) with a compound of the general formula:

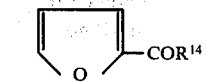
XXXVI (wherein R¹⁴ is as hereinbefore defined) by the procedures hereinbefore described for the condensation of compounds of formula XXXV with acyl halides or acid anhydride derived from compounds of general formula XXXIV.

Compounds of general formula XIII wherein R¹, R⁴, R⁵ and n are as hereinbefore defined and R⁶ represents a methoxy or ethoxy group, i.e. compounds of the general formula:

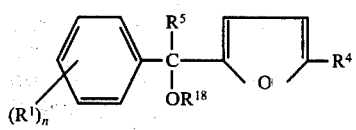
XXXVII (wherein R¹, R⁴, R⁵ and n are as hereinbefore defined and R¹⁸ represents a methyl or ethyl group), may be prepared by reacting a sodio derivative of a compound of general formula XIII wherein R¹, R⁴, R⁵ and n are as hereinbefore defined, and R⁶ represents a hydroxy group, i.e. a compound of general formula V (wherein R¹, R⁴, R⁵ and n are as hereinbefore defined) with a methyl or ethyl halide, e.g. methyl or ethyl iodide. The reaction is preferably effected at a temperature between 0° C. and ambient temperature in an inert organic solvent, e.g. dimethylformamide. The sodio derivative of the compound of general formula V may be prepared by reacting the compound of general formula V with sodium hydride at 0° C. in an inert organic solvent, e.g. dimethylformamide.

Compounds of general formula XIII, wherein R¹, R⁴, R⁵ and n are as hereinbefore defined and R⁶ represents a hydrogen atom, may be prepared from compounds of general formula V (wherein R¹, R⁴, R⁵ and n are as hereinbefore defined) by hydrogenation in the presence of a suitable hydrogenation catalyst, e.g. Raney copper, at an elevated temperature, e.g. at a temperature from 150° to 200° C., or by reduction with an alkali metal, e.g. sodium, in a lower alkanol, e.g. ethanol, at the boiling temperature of the reaction mixture.

Compounds of general formula XIII, wherein R¹, R⁴ and n are as hereinbefore defined, R⁵ represents an alkyl group and R⁶ represents a hydrogen atom, may be prepared by the reduction of the ethylenic double bond of a compound of the general formula:

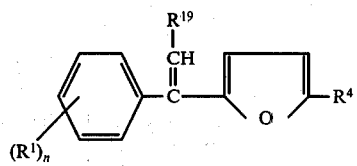
XXXVIII (wherein R¹, R⁴ and n are as hereinbefore defined and R¹⁹ represents a hydrogen atom or a straight- or branched-chain alkyl group containing from 1 to 5 carbon atoms) by hydrogenation in the presence of a hydrogenation catalyst, e.g. palladium on charcoal. Hydrogenation is preferably effected at ambient temperature and normal atmospheric pressure.

Compounds of general formula XXXVIII (wherein $R^1$, $R^4$, $R^{19}$ and $n$ are as hereinbefore defined) may be prepared by the dehydration of a compound of the general formula:

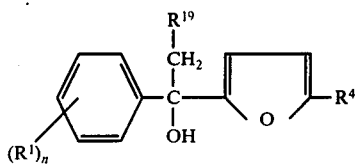  XXXIX wherein $R^1$, $R^4$, $R^{19}$ and $n$ are as hereinbefore defined. Dehydration may be conveniently effected by distilling the compound of general formula XXXIX or by treatment with a dehydrating agent, e.g. $POCl_3$ in pyridine.

Compounds of general formula XXXIX (wherein $R^1$, $R^4$, $R^{19}$ and $n$ are as hereinbefore defined) may be prepared by reacting a compound of general formula XXIV (wherein $R^1$, $R^4$ and $n$ are as hereinbefore defined) with an organomagnesium halide of the general formula:

$R^{19}CH_2MgX$    XL (wherein $R^{19}$ and X are as hereinbefore defined) or with an organolithium compound of the general formula:

$R^{19}CH_2Li$    XLI (wherein $R^{19}$ is as hereinbefore defined) in an inert organic solvent, for example a lower alkyl ether, e.g. diethyl ether, at a temperature between 0° C. and the boiling temperature of the reaction mixture, and hydrolysis of the organometallic compound thus obtained, for example by treatment with aqueous ammonium chloride solution.

Compounds of general formula V (wherein $R^1$, $R^4$, $R^5$ and $n$ are as hereinbefore defined) may be prepared by reacting a Grignard reagent of the general formula:

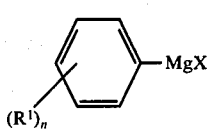  XLII (wherein $R^1$, X and $n$ are as hereinbefore defined) with a compound of the general formula:

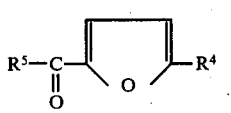  XLIII (wherein $R^4$ and $R^5$ are as hereinbefore defined) in an inert organic solvent, for example a lower alkyl ether, e.g. diethyl ether, at a temperature of from $-30°$ C. to the boiling temperature of the reaction mixture, and preferably at $-25°$ to $-20°$ C., and hydrolysis of the organomagnesium compound thus obtained, for example by treatment with aqueous ammonium chloride solution.

Compounds of general formula V (wherein $R^1$, $R^4$, $R^5$ and $n$ are as hereinbefore defined) may also be prepared by reacting a furyl lithium compound of the general formula:

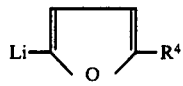  XLIV (wherein $R^4$ is as hereinbefore defined) with a ketone or aldehyde of the general formula:

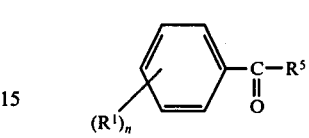  XLV (wherein $R^1$, $R^5$ and $n$ are as hereinbefore defined) in an inert organic solvent, for example a lower alkyl ether, e.g. diethyl ether, at a temperature of from 0° C. to the boiling temperature of the reaction mixture and hydrolysis of the organolithium compound thus obtained, for example by treatment with aqueous ammonium chloride solution.

Compounds of general formula XII (wherein $R^1$, $R^5$, $R^9$, Z and $n$ are as hereinbefore defined) may be prepared by treating a compound of the general formula:

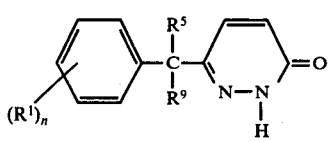  XLVI (wherein $R^1$, $R^5$, $R^9$ and $n$ are as hereinbefore defined) with phosphorus oxychloride or oxybromide at a temperature of from 50° to 110° C., optionally in the presence of an inert organic solvent but preferably in the presence of an excess of phosphorus oxychloride or oxybromide which serves as solvent for the reaction.

Compounds of general formula XLVI (wherein $R^1$, $R^5$, $R^9$ and $n$ are as hereinbefore defined) may be prepared by the dehydrogenation of a compound of the general formula:

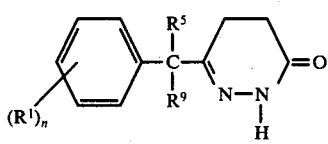  XLVII (wherein $R^1$, $R^5$, $R^9$ and $n$ are as hereinbefore defined) by treatment with a halogen, e.g. chlorine, iodine or, preferably, bromine, in an inert organic solvent, e.g. ethyl acetate, at a temperature between 0° C. and the boiling temperature of the reaction mixture.

Compounds of general formula XLVII (wherein $R^1$, $R^5$, $R^9$ and $n$ are as hereinbefore defined) may be prepared by reacting a compound of the general formula:

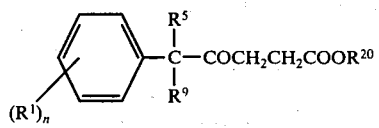  XLVIII (wherein $R^1$, $R^5$, $R^9$ and $n$ are as hereinbefore defined and $R^{20}$ represents a hydrogen atom or an alkyl group containing from 1 to 4 carbon atoms) with hydrazine hydrate in the presence of a lower alkanol, e.g. ethanol, at a temperature of from 20° C. to the boiling temperature of the reaction mixture.

Compounds of general formula XLVIII (wherein $R^1$, $R^5$, $R^9$, $R^{20}$ and $n$ are as hereinbefore defined) may be prepared by the condensation of a compound of the general formula:

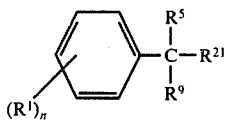
XLIX

[wherein $R^1$, $R^5$, $R^9$ and $n$ are as hereinbefore defined and $R^{21}$ represents a cyano group (—CN) or a group —COOR$^{20}$ (wherein $R^{20}$ is as hereinbefore defined)] with a succinic ester of the general formula:

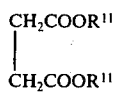
L (wherein $R^{11}$ is as hereinbefore defined) in the presence of a basic catalyst, e.g. sodium hydride or sodium methoxide, in an inert organic solvent, e.g. toluene or methanol, and preferably in the presence of sodium methoxide in methanol, followed by hydrolysis and decarboxylation of the product thus obtained by heating either in the presence of an inorganic acid and a lower alkanoic acid, e.g. hydrochloric acid in acetic acid, or in the presence of an inorganic acid, e.g. hydrochloric or hydrobromic acid, alone, at the boiling temperature of the reaction mixture, followed by, where appropriate, re-esterification of the product thus obtained by heating in the presence of an alkanol of the general formula:

$R^{11}OH$   LI (wherein $R^{11}$ is as hereinbefore defined) and an acid catalyst, preferably hydrogen chloride, at the boiling temperature of the reaction mixture.

According to a further feature of the present invention, the compounds of general formula I wherein $R^1$, $R^4$ and $n$ are as hereinbefore defined and $R^2$ and $R^3$ together represent a hydroxyimino group, i.e. compounds of the general formula:

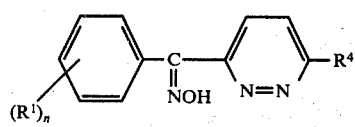
LII (wherein $R^1$, $R^4$ and $n$ are as hereinbefore defined), are prepared by reacting a compound of general formula X (wherein $R^1$, $R^4$ and $n$ are as hereinbefore defined) with hydroxylamine hydrochloride. The reaction is preferably effected in an aqueous lower alkanol, e.g. aqueous ethanol, at the boiling temperature of the reaction mixture in the presence of a base, conveniently sodium acetate.

According to a further feature of the present invention, the compounds of general formula I wherein $R^1$, $R^4$ and $n$ are as hereinbefore defined, $R^2$ represents a hydrogen atom or an alkyl group and $R^3$ represents a methoxy or ethoxy group, i.e. compounds of the general formula:

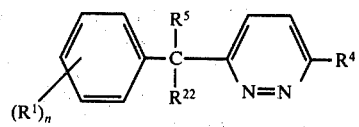
LIII (wherein $R^1$, $R^5$, $R^4$ and $n$ are as hereinbefore defined and $R^{22}$ represents a methoxy or ethoxy group), are prepared by reacting a compound of general formula IX (wherein $R^1$, $R^4$, $R^5$, $R^8$ and $n$ are as hereinbefore defined, and $R^8$ preferably represents a bromine or, more particularly, chlorine atom) with an alkali metal, e.g. sodium or potassium, methoxide or ethoxide.

The reaction is preferably effected either in methanol, when the reactant is a methoxide, or ethanol, when the reactant is an ethoxide, at the boiling temperature of the reaction mixture.

According to a further feature of the present invention, the compounds of general formula I wherein $R^1$ and $n$ are as hereinbefore defined, $R^2$ represents a hydrogen atom or an alkyl group, $R^3$ represents a hydrogen atom and $R^4$ represents a hydrogen atom, i.e. compounds of the general formula:

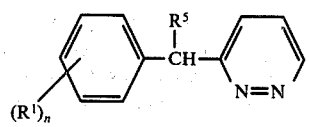
LIV (wherein $R^1$, $R^5$ and $n$ are as hereinbefore defined), are prepared from compounds of the general formula:

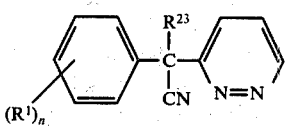
LV (wherein $R^1$ and $n$ are as hereinbefore defined and $R^{23}$ represents a hydrogen atom or a straight- or branched-chain alkyl group containing from 1 to 6 carbon atoms or a cyano group, $R^{23}$ being, respectively, a hydrogen atom or an alkyl group when $R^5$ in formula LIV represents a hydrogen atom or an alkyl group and $R^{23}$ being a cyano group when $R^5$ in formula LIV represents a hydrogen atom) by acid or, preferably, alkaline hydrolysis and decarboxylation of the mono- or di-carboxylic acid, obtained by the hydrolysis, by heating at an elevated temperature, e.g. at a temperature of from 150° to 250° C. Alkaline hydrolysis and decarboxylation of a compound of formula LV may be conveniently effected in a single step by treating the compound of formula LV with an alkali metal, e.g. potassium, hydroxide at an elevated temperature, and preferably at the reflux temperature of the reaction mixture, in a suitable inert organic solvent, e.g. ethylene glycol, in the presence of added water.

Compounds of general formula LV (wherein $R^1$, $R^{23}$ and $n$ are as hereinbefore defined) may be prepared by the reductive dehalogenation of a compound of the general formula:

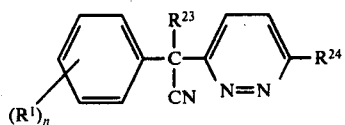

LVI wherein $R^1$, $R^{23}$ and $n$ are as hereinbefore defined and $R^{24}$ represents a chlorine or bromine atom. Reductive dehalogenation of a compound of general formula LVI is preferably effected by hydrogenation with hydrogen under moderate pressure, e.g. at a pressure of from 1 to 10 atmospheres, and a temperature of from 10° to 100° C., in the presence of a hydrogenation catalyst, e.g. palladium on charcoal, and a base, e.g. ammonium hydroxide or magnesium oxide, in an inert organic solvent, for example a lower alkanol, e.g. ethanol.

Compounds of general formula LVI (wherein $R^1$, $R^{23}$, $R^{24}$ and $n$ are as hereinbefore defined) may be prepared by reacting 3,6-dichloro- or 3,6-dibromopyridazine with a compound of the general formula:

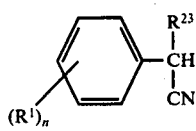

LVII (wherein $R^1$, $R^{23}$ and $n$ are as hereinbefore defined) in the presence of a base, preferably an aqueous alkali metal, e.g. sodium, hydroxide and in the presence of a suitable phase transfer catalyst, for example triethylbenzylammonium chloride or a 'crown' ether, e.g. 2,3,11,12-dibenzo-1,4,7,10,13,16-hexaoxacylooctadeca-2,11-diene.

Compounds of general formual LVII may be prepared by known methods.

Agriculturally-acceptable salts of the compounds of general formula I with acids may be prepared by conventional methods for the preparation of salts of organic bases, for example by reacting a compound of general formula I with an acid, e.g. hydrochloric acid, if desired in the presence of a suitable solvent, e.g. water or an aqueous alkanol. The salt which is formed is precipitated, if necessary after concentration of its solution, and is separated by filtration or decantation.

Agriculturally-acceptable salts of compounds of general formula I, wherein $R^1$ represents a carboxy group, with bases may be prepared by conventional methods for the preparation of salts of carboxylic acids, e.g. by treatment of the acid in aqueous, aqueous-alkanolic or alkanolic, e.g. ethanol, solution or suspension with the appropriate alkali metal or alkaline earth metal hydroxide, oxide, carbonate or bicarbonate or a strong amine. The salt which is formed is precipitated, if necessary after concentration of its solution, and is separated by filtration or decantation.

Agriculturally-acceptable salts of the compounds of general formula I thus obtained may be used in the preparation of herbicidal compositions herein described. If desired, solutions or suspensions of agriculturally-acceptable salts of compounds of general formula I obtained in the preparation of such salts as hereinbefore described may themselves be used as herbicidal compositions.

The following Examples illustrate the preparation of pyridazine derivatives of general formula I according to the present invention.

EXAMPLE 1

A solution of 3-chloro-6-(2-methylbenzyl)pyridazine (34 g.) in ethanol (370 ml.) containing aqueous ammonium hydroxide solution (s.g. 0.880; 38 ml.) was treated with hydrogen in the presence of palladium on charcoal (5% Pd) at ambient temperature and normal atmospheric pressure for 1.5 hours. After filtration, the filtrate was evaporated to dryness and the residue extracted with chloroform (3 × 100 ml.). The chloroform solution was washed with water, dried over magnesium sulphate and evaporated to dryness. The light brown solid thus obtained was triturated with n-hexane to give 3-(2-methylbenzyl)pyridazine (26 g.), m.p. 88°-89° C.

By proceeding in a similar manner but replacing the 3-chloro-6-(2-methylbenzyl)pyridazine by 6-benzyl-3-chloropyridazine (prepared as described in Netherlands Pat. No. 66-09504), 3-chloro-6-(2,6-dimethylbenzyl)pyridazine and 3-chloro-6-(2,4,6-trimethylbenzyl)pyridazine, there were prepared, respectively, 3-benzylpyridazine, m.p. 62°-64° C., 3-(2,6-dimethylbenzyl)pyridazine, m.p. 102°-103° C., and 3-(2,4,6-trimethylbenzyl)pyridazine, m.p. 110°-110.5° C.

3-Chloro-6-(2-methylbenzyl)pyridazine, 3-chloro-6-(2,6-dimethylbenzyl)pyridazine and 3-chloro-(2,4,6-trimethylbenzyl)pyridazine used as starting materials in the above preparations may be prepared as follows:

Diethyl succinate (510 g.) and 2-methylbenzyl cyanide [prepared according to the method of Meisenheimer et al, Ann. 468, 217 (1929); 155 g.] were added to a solution of sodium (42 g.) in dry methanol (585 ml.) at ambient temperature. The mixture was heated under reflux, with stirring, for 16 hours and excess methanol was then removed by distillation under reduced pressure. The residue was dissolved in a mixture of toluene (500 ml.) and water (2000 ml.). The aqueous layer was separated, acidified with concentrated sulphuric acid (50 ml.) and extracted with diethyl ether (3 × 800 ml.). The ethereal extract was washed with water, dried over sodium sulphate and evaporated to dryness to give ethyl 5-cyano-4-oxo-5-(2-methylphenyl)pentanoate (305 g.) in the form of a dark coloured oil.

By proceeding in a similar manner, but replacing the 2-methylbenzyl cyanide by 2,6-dimethylbenzyl cyanide [prepared as described by Rasen and Eastham, J.A.C.S., 82, 1349 (1960)] and 2,4,6-trimethylbenzyl cyanide [prepared as described in Org. Synth, 25, 65 (1945)], there were obtained, respectively, ethyl 5-cyano-5-(2,6-dimethylphenyl)-4-oxopentanoate and ethyl 5-cyano-5-(2,4,6-trimethylphenyl)-4-oxopentanoate.

Undistilled ethyl 5-cyano-4-oxo-5-(2-methylphenyl)pentanoate (prepared by the procedure described above; 773 g.) was heated under reflux with hydrobromic acid (48-50%; 1550 ml.) for 3 hours. On cooling, the reaction mixture separated into two layers. The lower, aqueous phase was separated and extracted with chloroform (3 × 500 ml.). The chloroform extract was added to the upper, organic layer of the reaction mixture. The chloroform solution (about 2 liters) thus obtained was washed with water (3 × 200 ml.) and evaporated to give 5-(2-methylphenyl)-4-oxopentanoic acid (535 g.) in the form of a dark coloured oil.

By proceeding in a similar manner but replacing the ethyl 5-cyano-4-oxo-5-(2-methylphenyl)pentanoate by ethyl 5-cyano-5-(2,6-dimethylphenyl)-4-oxopentanoate and ethyl 5-cyano-5-(2,4,6-trimethylphenyl)-4-oxopentanoate (prepared as described above), there were obtained, respectively, 5-(2,6-dimethylphenyl)-4-oxopentanoic acid and 5-(2,4,6-trimethylphenyl)-4-oxopentanoic acid.

5-(2-Methylphenyl)-4-oxopentanoic acid (prepared as described above; 535 g.) was heated under reflux for 1 hour in methanol (5.5 liters) through which was passed gaseous hydrogen chloride. The flow of hydrogen chloride was then stopped and the solution was heated for a further 2 hours. The solution was then evaporated to give a dark coloured oil which was dissolved in diethyl ether (1500 ml.), washed with water and aqueous sodium bicarbonate solution, dried over sodium sulphate and distilled to give methyl 5-(2-methylphenyl)-4-oxopentanoate (248 g.), in the form of a clear yellow oil, b.p. 170°–200° C./0.7–1.0 mm.Hg.

Methyl 5-(2-methylphenyl)-4-oxopentanoate (prepared as described above; 28.2 g.), hydrazine hydrate (7.2 ml.), triethylamine (18 ml.) and ethanol (18 ml.) were heated under reflux for 40 minutes. After cooling, the solution was filtered to remove colourless crystals. The filtrate was evaporated to dryness and the residue was heated under reflux for 40 minutes with hydrazine hydrate (5 ml.), ethanol (11 ml.) and triethylamine (11 ml.). After cooling, the solution was filtered to give a second crop of colourless crystals. The filtrate was evaporated to dryness and the residue was heated under reflux for 40 minutes with hydrazine hydrate (5 ml.), ethanol (11 ml.) and triethylamine (11 ml.). After cooling, the solution was filtered to give a third crop of colourless crystals.

The three crops of crystals thus obtained were combined, washed with cold ethanol (30 ml.) and diethyl ether (30 ml.) and dried to give 6-(2-methylbenzyl)2,3,4,5-tetrahydropyridaz-3-one (19.2 g.), m.p. 118°–120° C.

By proceeding in a similar manner but replacing the methyl 5-(2-methylphenyl)-4-oxopentanoate by 5-(2,6-dimethylphenyl)-4-oxopentanoic acid and 5-(2,4,6-trimethylphenyl)-4-oxopentanoic acid (prepared as described above), there were obtained, respectively, 6-(2,6-dimethylbenzyl)-2,3,4,5-tetrahydropyridaz-3-one, m.p. 123°–125° C., and 2,3,4,5-tetrahydro-6-(2,4,6-trimethylbenzyl)pyridaz-3-one, m.p. 149°–151° C.

A solution of bromine (5.3 ml.) in ethyl acetate (5.3 ml.) was added over 15 minutes to a refluxing solution of 6-(2-methylbenzyl)-2,3,4,5-tetrahydropyridaz-3-one (prepared as described above; 19.2 g.) in ethyl acetate (150 ml.). Heating under reflux was continued for a further 15 minutes. The reaction mixture was then cooled to 0° C. and filtered. Solid 2,3-dihydro-6-(2-methylbenzyl)pyridaz-3-one hydrobromide thus obtained was washed with n-hexane, dried in vacuo, added to an excess of aqueous sodium bicarbonate solution, stirred with a magnetic stirrer for one hour and filtered. The residue was washed with water and dried in air at 60° C. to give 2,3-dihydro-6-(2-methylbenzyl)-pyridaz-3-one (13.9 g.) in the form of a fawn coloured powder, m.p. 139°–141° C.

By proceeding in a similar fashion but replacing the 6-(2-methylbenzyl)-2,3,4,5-tetrahydropyridaz-3-one by 6-(2,6-dimethylbenzyl)-2,3,4,5-tetrahydropyridaz-3-one and 2,3,4,5-tetrahydro-6-(2,4,6-trimethylbenzyl)-pyridaz-3-one (prepared as described above), there were obtained, respectively, 2,3-dihydro-6-(2,6-dimethylbenzyl)pyridaz-3-one, m.p. 162°–169° C., and 2,3-dihydro-6-(2,4,6-trimethylbenzyl)pyridaz-3-one, m.p. 156°–157° C.

2,3-Dihydro-6-(2-methylbenzyl)pyridaz-3-one (prepared as described above; 36 g.) and phosphorus oxychloride (120 ml.) were heated together on a steam bath to 90° C. The dark red solution thus obtained was immediately cooled to 10°–15° C., diluted with acetone (125 ml.) and added to a stirred solution of acetone and aqueous ammonium hydroxide solution (s.g. 0.880) (1:1; 1000 ml.) maintained at a temperature of from 0° to 20° C. by strong cooling. The mixture was then diluted with water (1000 ml.). A light brown coloured solid was precipitated, filtered off, dried and dissolved in toluene (200 ml.). The toluene solution was filtered and the filtrate evaporated to dryness to give 3-chloro-6-(2-methylbenzyl)pyridazine (34 g.) in the form of an off-white coloured solid, m.p. 73.5° C.

By proceeding in a similar fashion but replacing the 2,3-dihydro-6-(2-methylbenzyl)pyridaz-3-one by 2,3-dihydro-6-(2,6-dimethylbenzyl)pyridaz-3-one and 2,3-dihydro-6-(2,4,6-trimethylbenzyl)pyridaz-3-one (prepared as described above) there were obtained, respectively, 3-chloro-6-(2,6-dimethylbenzyl)pyridazine, m.p. 125°–127° C., and 3-chloro-6-(2,4,6-trimethylbenzyl)-pyridazine, m.p. 143°–145° C.

EXAMPLE 2

A solution of (±) 3-α-chlorobenzylpyridazine (2.05 g.) in ethanol (50 ml.) was treated with hydrogen, in the presence of magnesium oxide (0.4 g.) and palladium on charcoal (5% Pd; 0.2 g.), for 1 hour at ambient temperature and normal atmospheric pressure. The solution was then filtered and the filtrate was evaporated to dryness. The residue was dissolved in hot chloroform (100 ml.), cooled, washed with water (50 ml.), dried over magnesium sulphate and evaporated to give 3-benzylpyridazine (1.6 g.), m.p. 61°–64° C., in the form of a light brown coloured solid.

By proceeding in a similar fashion, but replacing the (±) 3-α-chlorobenzylpyridazine by (±) 3-(α,2,4-trichloro)benzylpyridazine, there was obtained 3-(2,4-dichlorobenzyl)pyridazine, m.p. 67°–69° C.

(±) 3-α-Chlorobenzylpyridazine and (±) 3-(α,2,4-trichloro)benzylpyridazine, used as starting materials in the above preparations, may be prepared as follows:

Pyridazine-3-carboxylic acid [prepared as described by Leanza, Becker and Rogers, J.A.C.S., 75, 4086 (1953); 18.6 g.] was mixed with benzaldehyde (44 g.) and p-cymene (360 ml.) and decarboxylated by heating for 3 hours at 135° C. The hot solution was then filtered, cooled and the precipitate collected to give (±) 3-α-hydroxybenzylpyridazine (5.2 g.), m.p. 130°–135° C., in the form of fawn coloured needles.

By proceeding in a similar fashion but replacing the benzaldehyde by 2,4-dichlorobenzaldehyde, there was obtained (±) 3-(2,4-dichloro-α-hydroxybenzyl)pyridazine, m.p. 130°–132° C.

Gaseous hydrogen chloride was passed at 0° C. into a magnetically-stirred solution of 3-α-hydroxybenzylpyridazine (prepared as described above; 7.44 g.) in dry toluene (400 ml.). Thionyl chloride (8 ml.) was then added at 0° C. and the reaction mixture was stirred at 5° C. for 2 hours and then at ambient temperature for 16 hours. The excess of thionyl chloride was removed by repeated evaporations with toluene. The residue was diluted with diethyl ether and ice and brought to pH 8 by the addition of aqueous sodium bicarbonate solution. The aqueous layer was separated and extracted sufficiently with diethyl ether (4 × 500 ml.) to dissolve all solid material.

The ether extracts were combined, dried over sodium sulphate and evaporated to give an off-white coloured solid, which was recrystallised from cyclohexane (400 ml.) to give (±) 3-α-chlorobenzylpyridazine (6.3 g.), mp. 110°-112° C., in the form of colourless needles.

By proceeding in a similar fashion, but replacing the 3-α-hydroxybenzylpyridazine by (±) 3-(2,4-dichloro-α-hydroxybenzyl)pyridazine (prepared as described above), there was obtained (±) 3-(α,2,4-trichloro)benzylpyridazine, in the form of a dark coloured oil which was subsequently used without further purification.

EXAMPLE 3

A mixture of 2-(2-methylbenzyl)furan (5.2 g.), anhydrous sodium carbonate (12.8 g.) and methanol (120 ml.) was stirred at −2° C. during the addition, over 40 minutes, of a solution of bromine (1.6 ml.; 9.3 g.) in methanol (24 ml.). The mixture was stirred for a further 5 minutes, diluted with water (300 ml.) and extracted with toluene (4 × 35 ml.). The combined toluene extracts were dried over magnesium sulphate and evaporated to dryness to give crude 2-(2-methylbenzyl)-2,5-dimethoxy-2,5-dihydrofuran (7.2 g.) in the form of a pale brown coloured oil, which was then heated under reflux with phenol (20 g.) and hydrazine hydrate (2.6 ml.) for 70 hours in an oil bath at 120° C. Hydrochloric acid (100 ml. of 2N and 10 ml. of concentrated hydrochloric acid) was added and the mixture was steam-distilled to remove phenol. The mixture was then cooled and extracted with diethyl ether (50 ml.). The ether solution was extracted with N hydrochloric acid (5 × 10 ml.). Dissolved diethyl ether was removed from the combined aqueous acid extracts by the passage of a stream of air. The aqueous acid solution was then treated with charcoal, filtered, neutralised with solid sodium bicarbonate, basified by the addition of aqueous sodium hydroxide solution (2N; 10 ml.) and extracted with chloroform (5 × 20 ml.). The combined chloroform extracts were washed with water, dried over magnesium sulphate and distilled to give 3-(2-methylbenzyl)pyridazine (2.7 g.) as a white solid, m.p. 86°-89° C. [b.p. 115°-125° C. (bath temperature)/0.1 mm.Hg], the melting point of which was raised to 89°-91° C. by dissolution in 2N hydrochloric acid, filtration and precipitation from the clarified solution by the addition of solid sodium carbonate.

By proceeding in a similar fashion but replacing the 2-(2-methylbenzyl)furan by the appropriate 2-benzylfurans indicated below, there were prepared: 3-benzylpyridazine [b.p. 119°-124° C. (bath temperature)/0.15 mm.Hg; m.p. 62°-64° C., raised to 65°-67° C. by recrystallisation from diethyl ether] from 2-benzylfuran (prepared according to Mndzhoyan and Afrikyan, Dorklady Akad; Nauk Armyan SSR, 1957, 25, 201);

3-(2-chlorobenzyl)pyridazine, (b.p. 168°-170° C./0.2 mm.Hg;m.p. 38°-40° C.) from 2-(2-chlorobenzyl)furan;

3-(3-chlorbenzyl)pyridazine (b.p. 110°-115° C./0.2 mm.Hg) from 2-(3-chlorobenzyl)furan;

3-(4-chlorobenzyl)pyridazine (b.p. 160°-170° C./0.1 mm.Hg; m.p. 64°-65° C.) from 2-(4-chlorobenzyl)furan [prepared according to the method of Mndzhoyan et al, Arm. Khim. Zh. 19(10), 793 (1966)];

3-(2-fluorobenzyl)pyridazine (b.p. 125°-130° C./0.1 mm.Hg) from 2-(2-fluorobenzyl)furan;

3-(2-bromobenzyl)pyridazine (b.p. 165°-170° C./0.1 mm.Hg) from 2-(2-bromobenzyl)furan;

3-(2-methoxybenzyl)pyridazine (b.p. 145°-150° C./0.1 mm.Hg; m.p. 45°-50° C.) from 2-(2-methoxybenzyl)furan [previously described by Tukana, Nippon Kagaku Zasshi, 80, 313 (1939)];

3-(2-ethoxybenzyl)pyridazine (b.p. 130°-135° C./0.1 mm.Hg) from 2-(2-ethoxybenzyl)furan;

3-(3-methylbenzyl)pyridazine (b.p. 129°-131° C./0.2 mm.Hg) from 2-(3-methylbenzyl)furan;

3-(4-methylbenzyl)pyridazine (m.p. 103°-105° C. after recrystallisation from cyclohexane) from 2-(4-methylbenzyl)furan [prepared according to Mndzhoyan et al., Dorklady Akad. Nauk. Armyan SSR, 1958 27, 301];

3-(2,6-dichlorobenzyl)pyridazine (m.p. 65° C.) from 2-(2,6-dichlorobenzyl)furan;

3-(3,4-dichlorobenzyl)pyridazine (m.p. 91°-92° C.) from 2-(3,4-dichlorobenzyl)furan;

3-(2,3-dimethylbenzyl)pyridazine (m.p. 93°-95° C.; b.p. 163°-165° C./0.1 mm.Hg) from 2-(2,3-dimethylbenzyl)furan;

3-(2,4-dimethylbenzyl)pyridazine (m.p. 96°-98° C.; b.p. 178°-180° C./0.8 mm.Hg) from 2-(2,4-dimethylbenzyl)furan;

3-(2,5-dimethylbenzyl)pyridazine (b.p. 145° C./0.25 mm.Hg; m.p. 86°-88° C.) from 2-(2,5-dimethylbenzyl)furan;

3-(3,5-dimethylbenzyl)pyridazine (b.p. 143° C./0.25 mm.Hg; m.p. 51°-54° C.) from 2-(3,5-dimethylbenzyl)furan;

3-(2-ethylbenzyl)pyridazine (b.p. 149°-151° C./0.2 mm.Hg; m.p. 41°-42° C.) from 2-(2-ethylbenzyl)furan;

(±) 3-(1-phenylethyl)pyridazine (b.p. 135°-137° C./0.2 mm.Hg; m.p. 47°-49° C.) from (±) 2-(1-phenylethyl)furan;

3-(3,4-dimethylbenzyl)pyridazine (b.p. 163°-155° C./0.25 mm.Hg; m.p. 93°-95° C.) from 2-(3,4-dimethylbenzyl)furan;

3-(2-methylthiobenzyl)pyridazine (b.p. 160°-170° C./0.1 mm.Hg; m.p. 62.5°-64.5° C.) from 2-(2-methylthiobenzyl)furan;

3-(4-chloro-2-methylbenzyl)pyridazine (b.p. 160°-165° C./0.25 mm.Hg; m.p. 92°-94.5° C.) from 2-(4-chloro-2-methylbenzyl)furan;

3-(2-chloro-4-methylbenzyl)pyridazine (b.p. 145°-150° C./0.2 mm.Hg; m.p.75°-77° C.) from 2-(2-chloro-4-methylbenzyl)furan;

3-(2-isopropylbenzyl)pyridazine (m.p. 93°-95° C. after recrystallisation from cyclohexane) from 2-(2-isopropylbenzyl)furan;

(±) 3-[1-(2-methylphenyl)ethyl]pyridazine (b.p. 134°-136° C./0.2 mm. Hg; m.p. 73°-74° C.) from (±) 2-[1-(2-methylphenyl)ethyl]furan;

(±) 3-(1-phenylpropyl)pyridazine (m.p. 50°-51° C. after recrystallisation from toluene/light petroleum b.p. 40°-60° C.) from (±) 2-(1-phenylpropyl)furan;

(±) 3-[1-(3-methylphenyl)ethyl]pyridazine (b.p. 165°-170° C./0.1 mm.Hg;) from (±) 2-[1-(3-methylphenyl)ethyl]-furan;

(±) 3-[1-(2-chlorophenyl)ethyl]pyridazine (b.p. 155°–165° C./0.05 mm.Hg; m.p. 44°–46° C.) from (±) 2-[1-(2-chlorophenyl)ethyl]furan;

(±) 3-[1-(3-chlorophenyl)ethyl]pyridazine (b.p. 170°–180° C./0.05 mm.Hg) from (±) 2-[1-(3-chlorophenyl)-ethyl]furan;

(±) 3-[1-(4-chlorophenyl)ethyl]pyridazine (b.p. 145°–150° C./0.1 mm.Hg; m.p. 43°–44° C. after recrystallisation from diethyl ether/n-hexane) from (±) 2-[1-(4-chlorophenyl)ethyl]furan;

(±) 3-[1-(2-fluorophenyl)ethyl]pyridazine (b.p. 145°–150° C./0.05 mm.Hg; m.p. 57°–58° C.) from (±) 2-[1-(2-fluorophenyl)ethyl]furan;

(±) 3-[1-(2-bromophenyl)ethyl]pyridazine (b.p. 165°–170° C./0.05 mm.Hg) from (±) 2-[1-(2-bromophenyl)-ethyl]furan;

(±) 3[1-(2-methoxyphenyl)ethyl]pyridazine (b.p. 145°–150° C./0.1 mm.Hg; m.p. 69°–71° C.) from (±) 2[1-(2-methoxyphenyl)ethyl]furan;

(±) 3-[1-(2-ethylphenyl)ethyl]pyridazine (b.p. 145°–155° C./0.2 mm.Hg) from (±) 2-[1-(2-ethylphenyl)-ethyl]furan;

(±) 3-[1-(2,3-dimethylphenyl)ethyl]pyridazine (m.p. 99°–100° C. after recrystallisation from cyclohexane) from (±) 2-[1-(2,3-dimethylphenyl)ethyl]furan;

(±) 3-[1-(2,3-dimethylphenyl)ethyl]pyridazine (b.p. 150°–155° C./0.05 mm.Hg; m.p. 81°–82° C.) from (±) 2-[1-(2,4-dimethylphenyl)ethyl]furan;

(±) 3-[1-(2,4-dichlorophenyl)ethyl]pyridazine (b.p. 138° C./0.1 mm.Hg) from (±) 2-[1-(2,4-dichlorophenyl)-ethyl]furan;

(±) 3-[1-(4-chloro-2-methylphenyl)ethyl]pyridazine (b.p. 170°–175° C./0.1 mm.Hg; m.p. 72°–74° C.) from (±) 2-[1-(4-chloro-2-methylphenyl)ethyl]furan;

(±) 3-[1-(2-methylphenyl)propyl]pyridazine (b.p. 130° C./0.05 mm.Hg; m.p. 45°–47° C.) from (±) 2-[1-(2-methylphenyl)propyl]furan;

(±) 3-(α-hydroxybenzyl)pyridazine (m.p. 140°–143° C.) from (±) 2-(α-hydroxybenzyl)furan;

(±) 3-(2-chloro-α-hydroxybenzyl)pyridazine (m.p. 118°–119° C.) from (±) 2-(2-chloro-α-hydroxybenzyl)furan;

(±) 3-(2-bromo-α-hydroxybenzyl)pyridazine (m.p. 138°–140° C. after recrystallisation from toluene) from (±) 2-(2-bromo-α-hydroxybenzyl)furan;

(±) 3-(α-hydroxy-2-methylbenzyl)pyridazine (b.p. 195°–205° C./0.1 mm.Hg; m.p. 86°–88° C.) from (±) 2-(α-hydroxy-2-methylbenzyl)furan;

(±) 3-(α-hydroxy-2-methoxybenzyl)pyridazine (b.p. 190°–197° C./0.5 mm.Hg; m.p. 94°–100° C.) from (±) 2-(α-hydroxy-2-methoxybenzyl)furan;

(±)3-(2-ethyl-α-hydroxybenzyl)pyridazine (m.p. 70°–72° C. after recrystallization from cyclohexane) from (±) 2-(2-ethyl-α-hydroxybenzyl)furan;

(±) 3-(2,3-dichloro-α-hydroxybenzyl)pyridazine (m.p. 160°–162° C. after recrystallisation from toluene) from (±) 2-(2,3-dichloro-α-hydroxybenzyl)furan;

(±) 3-(2,5-dichloro-α-hydroxybenzyl)pyridazine (m.p. 147°–148° C.) from (±) 2-(2,5-dichloro-α-hydroxybenzyl)furan;

(±) 3-(α-methoxybenzyl)pyridazine (b.p. 130° C./0.05 mm.Hg) from (±) 2-(α-methoxybenzyl)furan;

(±) 3-(α-ethoxybenzyl)pyridazine (b.p. 175°–180° C./0.5 mm.Hg) from (±) 2-(α-ethoxybenzyl)furan;

(±) 3-(2-chloro-α-methoxybenzyl)pyridazine (b.p. 145°–150° C./0.1 mm.Hg) from (±) 2-(2-chloro-α-methoxybenzyl)furan;

(±) 3-(2-bromo-α-methoxybenzyl)pyridazine (b.p. 142°–150° C./0.05 mm.Hg) from (±) 2-(2-bromo-α-methoxybenzyl)furan;

(±) 3-(2-methyl-α-methoxybenzyl)pyridazine (b.p. 135°–138° C./0.05 mm.Hg) from (±) 2-(2-methyl-α-methoxybenzyl)furan and (±) 3-(2-ethyl-α-methoxybenzyl)pyridazine (b.p. 152°–153° C./0.5 mm.Hg) from (±) 2-(2-ethyl-α-methoxybenzyl)furan.

2-Benzylfurans used as starting materials in the above preparations may be prepared by the following procedures:

a. A mixture of 2-methylbenzyl bromide [prepared as described by Radziszewaki and Wispek, Ber, 15, 1747 (1882); 18.5 g.], methyl 2-furoate (15.3 g.) and anhydrous ferric chloride (0.3 g.) in dry carbon tetrachloride (25 ml.) was heated on a steam bath under reflux for 18 hours and then distilled to give crude methyl 5-(2-methylbenzyl)-2-furoate (7.7 g.) in the form of a pale brown coloured oil, b.p. 120°–145° C./0.1 mm.Hg, suitable for use as a starting material in procedures hereinafter described.

b. A mixture of 2-methylbenzyl chloride [prepared as described by Voronkov and Popova, Latv. P.S.R. Zinat. Akad. Vestis Kim. Sev. 1970(5), 595; 62 g.], methyl 2-furoate (114 g.) and anhydrous ferric chloride (1.4 g.) in dry carbon tetrachloride (120 ml.) was heated on a steam bath under relfux for 18 hours. The solution was then evapoated to dryness. The residue was dissolved in chloroform, washed with 2N hydrochloric acid and water, dried over magnesium sulphate and distilled to give methyl 5-(2-methylbenzyl)-2-furoate (50 g.) in the form of a yellow coloured oil, b.p. 140°–170° C./0.1–0.5 mm.Hg.

By proceeding in a similar fashion but replacing the 2-methylbenzyl chloride by 2-chlorobenzyl chloride [prepared as described by Olivier, Rec. Trav. Chim., 41, 308 (1922)], 2-bromobenzyl chloride [prepared as described by Jacobs and Heidelberger, J. Biol. Chem., 20, 659 (1915)], 2-fluorobenzyl chloride [prepared as described by Binnett and Jones, J.C.S. (1935), 1815], 2-ethoxybenzyl chloride [prepared as described by Pschorr and Zeidler, Ann., 373, 76 ( 1910)], 2,6-dichlorobenzyl chloride [prepared as described by Austin and Johnson, J.A.C.S., 54, 647 (1932)], 3,4-dichlorobenzyl chloride [prepared as described by Beilstein and Kuhlberg, Ann., 146, 326 (1868)], 2,3-dimethylbenzyl chloride [prepared as described by Smith and Spillam, J.A.C.S., 62, 2640 (1940)], 2,4-dimethylbenzyl chloride [prepared as described by von Braun and Nelles, Ber., 67, 1094 (1934)], 2,5-dimethylbenzyl chloride, 2-ethylbenzylchloride (prepared as described by Zanten and Nauta, Rec. Trav. Chim., 1960, 79, 1211), (±) 1-phenylethyl chloride [prepared as described by von Braun and Nelles, Ber, 67, 1094 (1934)], 3,4-dimethylbenzyl chloride [prepared as described by Benington, Morin & Clarke, J. Org. Chem., 1960, 25, 2066], 2-methylthiobenzyl chloride [previously reported by Grice and Owen, J.C.S. 1963, (1947)], 4-chloro-2-methylbenzyl chloride [previously reported by Osdene et al., J. Med. Chem., 10, 434 (1967)], 2-chloro-4-methylbenzyl chloride [previously reported by Wukae & Konishi, Yuki Gôsei Kagaku Kyôkaishi 17, 697 (1959)], 1-(2-methylphenyl)ethyl chloride [prepared as described by Baddeley and Chadwick, J.C.S., 1952, 372], 1-phenylpropyl chloride [prepared as described by Pickard & Kenyon, J.C.S. 1911, 71], 1-(3-methylphenyl)ethyl chloride [prepared as described by Lewis, Johnson & Coppinger, J.A.C.S., 81, 3140 (1959)], 1-(2-chlorophenyl)ethyl chloride [prepared as described by Mamedov et al., Azerb. Khim. Zh, 5, 50 (1967)], 1-(3-chlorophenyl)ethyl chloride [prepared as described by Emerson & Lucas, J.A.C.S. 70, 1180 (1948)], 1-(4-chlorophenyl)ethyl chloride [prepared as described by Woodcock, J.C.S. 1949, 203], 1-(2-fluorophenyl)ethyl chloride, 1-(2-bromophenyl)ethyl chloride [prepared as described by Marvel & Moon, J.A.C.S. 62, 45 (1940)], 1-(2,3-dimethylphenyl)ethyl chloride, 1-(2,4-dimethylphenyl)ethyl chloride and 1-(2,4-dichlorophenyl)ethyl chloride, there were obtained respectively:

methyl 5-(2-chlorobenzyl)-2-furoate, b.p. 160°-180° C./0.1 mm.Hg;

methyl 5-(2-bromobenzyl)-2-furoate, b.p. 160° C./0.1 mm.Hg;

methyl 5-(2-fluorobenzyl)-2-furoate, b.p. 130°-145° C./0.25 mm.Hg;

methyl 5-(2-ethoxybenzyl)-2-furoate, b.p. 145°-165° C./0.2 mm.Hg.

methyl 5-(2,6-dichlorobenzyl)-2-furoate, b.p. 180°-220° C./ 0.1-0.2 mm.Hg;

methyl 5-(3,4-dichlorobenzyl)-2-furoate, b.p. 160°-210° C./0.2 mm.Hg;

methyl 5-(2,3-dimethylbenzyl)-2-furoate, b.p. 155°-158° C./0.2 mm.Hg;

methyl 5-(2,4-dimethylbenzyl-2-furoate, b.p. 146°-150° C./0.3 mm.Hg;

methyl 5-(2,5-dimethylbenzyl)-2-furoate, b.p. 147°-152° C./0.25 mm.Hg;

methyl 5-(2-ethylbenzyl)-2-furoate, b.p. 141°-146° C./0.25 mm.Hg;

methyl (±) 5-(1-phenylethyl)-2-furoate, b.p. 140° C./0.14 mm.Hg;

methyl 5-(3,4-dimethylbenzyl)-2-furoate, b.p. 143°-148° C./0.1 mm.Hg;

methyl 5-(2-methylthiobenzyl)-2-furoate, b.p. 190°-192°C./0.6 mm.Hg;

methyl 5-(4-chloro-2-methylbenzyl)-2-furoate, b.p. 144°-150° C./0.05 mm.Hg;

methyl 5-(2-chloro-4-methylbenzyl)-2-furoate, b.p. 140°-165° C./0.12 /mm.Hg;

methyl (±) 5-[1-(2-methylphenyl)ethyl]-2-furoate, b.p. 125°-128° C/0.15 mm.Hg;

methyl (±) 5-(1-phenylpropyl)-2-furoate, b.p. 140°-160° C./0.2 mm.Hg;

methyl (±) 5-[1-(3-methylphenyl)ethyl]-2-furoate, b.p. 125°-150° C./0.1 mm.Hg;

methyl (±) 5-[1-(2-chlorophenyl)ethyl]-2-furoate, b.p. 130°-170° C./0.2 mm.Hg;

methyl (±) 5-[1-(3-chlorophenyl)ethyl]-2-furoate, b.p. 155°-175° C./0.1 mm.Hg;

methyl (±) 5-[1-(4L -chlorophenyl)ethyl]-2-furoate, b.p. 160°-180° C./0.2 mm.Hg;

methyl (±) 5-[1-(2-fluorophenyl)ethyl]-2-furoate, b.p. 140°-150° C./0.05 mm.Hg;

methyl (35 ) 5-[1-(2-bromophenyl)ethyl]-2-furoate, b.p. 163°-187°]C./0.2 mm.Hg;

methyl (±) 5-[1-(2,3-dimethylphenyl)ethyl]-2-furoate, b.p. 140°-180° C./0.1 mm.Hg;

methyl (35 ) 5-[1-(2,4-dimethylphenyl)ethyl]-2-furoate, b.p. 135°-175° C./0.5 mm.Hg, and methyl (±) 5-[1-(2,4-dichlorophenyl)ethyl]-2-furoate, b.p. 180°-200° C./0.1 mm.Hg.

c. A mixture of 2-methylbenzoyl chloride (prepared as described by Frankland and Ashton, Trans. Chem. Soc. 1899, 75, 494; 77 g.), methyl 2-furoate (83 g.), anhydrous ferric chloride (1.5 g.) and carbon tetrachloride (125 ml.) was heated under reflux on a steam bath for 7.5 hours and then distilled to give methyl 5-(2-methylbenzoyl)-2-furoate (110 g.) in the form of a colourless oil, b.p. 170° C./0.2 mm.Hg.

By proceeding in a similar fashion but replacing the 2-methylbenzoyl chloride by 2-chlorobenzoyl chloride [prepared as described by Emmerling, Ber. 8, 883 (1875)], 3-chlorobenzyl chloride [prepared as described by Limprikt and von Uslar, Ann, 102, 263 (1857)], 3-methylbenzoyl chloride [prepared as described by Frankland and Aston, Trans. Chem. Soc., 1899, 75, 494], 3,4-dichlorobenzoyl chloride [prepared as described by Cohen and Briggs, J.C.S., (1903), 83, 1213], 2-bromobenzoyl chloride [prepared as described by Schotten, Ber., 21, 2251 (1888)], 2-ethylbenzoyl chloride [prepared as described by Giebe, Ber., 29, 2535 (1896)], 4-chloro-2-methylbenzoyl chloride [prepared as described by Verbeest and Slootmaekers, Bull. Soc. Chim. Belg., 77, 287 (1968)], 2,3-dimethylbenzoyl chloride [prepared as described by Bergmann and Ikan, J.A.C.S., 80, 5803 (1958)], 2,5-dimethylbenzoyl chloride [prepared as described by van Zanten and Nauta, Rec. Trav. Chem. 79, 1211 (1960)] and 3,5-dimethylbenzoyl chloride [prepared as described by Gryszkiewiez-Trochimowski and Schmidt, Bull. Soc. Chim., France, 593 (1948)], respectively, there were obtained:

methyl 5-(2-chlorobenzoyl)-2-furoate, mp. 70°-71° C.;

methyl 5-(3-chlorobenzoyl)-2-furoate, b.p. 170°-180° C./0.1 mm.Hg;

methyl 5-(3-methylbenzoyl)-2-furoate, b.p. 155°-160° C./0.2 mm.Hg;

methyl 5-(3,4-dichlorobenzoyl)-2-furoate, m.p. 99°-101° C;

methyl 5-(2-bromobenzoyl)-2-furoate, b.p. 173°-215° C./0.1 mm.Hg;

methyl 5-(2-ethylbenzoyl)-2-furoate, b.p. 175°-195° C./0.05 mm.Hg;

methyl 5-(4-chloro-2-methylbenzoyl)-2-furoate, m.p. 102°-103° C.;

methyl 5-(2,3-dimethylbenzoyl)-2-furoate, b.p. 183°-188° C./0.5 mm.Hg;

methyl 5-(2,5-dimethylbenzoyl)-2-furoate, m.p. 116°-118° C., and methyl 5-(3,5-dimethylbenzoyl)-2-furoate, b.p. 188°-196° C./0.3 mm.Hg.

d. A cold solution of potassium hydroxide (2.2 g.) in water (4 ml.) and methanol (8 ml.) was added to a solution of methyl 5-(2-methylbenzyl)-2-furoate [prepared as described in (a) or (b) above; 7.7 g.] in methanol (20 ml.) and the mixture was allowed to stand overnight at ambient temperature. The solution was then evaporated to dryness. The residue was dissolved in water (75 ml.) and filtered. The filtrate was acidified by the dropwise addition of concentrated hydrochloric acid, with stirring, to precipitate 5-(2-methylbenzyl)-2-furoic acid (4.5 g.) in the form of a white solid, m.p. 138°-140° C.

By proceeding in a similar fashion but replacing the methyl 5-(2-methylbenzyl-2-furoate by the appropriate methyl 5-benzyl-2-furoate prepared as described in (b) above there were obtained:

5-(2-chlorobenzyl)-2-furoic acid, m.p. 135°-139° C.;

5-(2-bromobenzyl)-2-furoic acid, m.p. 141°-143° C.;

5-(2-fluorobenzyl)-2-furoic acid, m.p. 132°-134° C.;

5-(2-ethoxybenzyl)-2-furoic acid, m.p. 128°–130° C.;
5-(2,6-dichlorobenzyl)-2-furoic acid, m.p. 174°–177° C.;
5-(2,3-dimethylbenzyl)-2-furoic acid, m.p. 148°–150° C. (after recrystallisation from aqueous isopropanol);
5-(2,4-dimethylbenzyl)-2-furoic acid, m.p. 154°–156° C.;
5-(2,5-dimethylbenzyl)-2-furoic acid, m.p. 127°–129° C.;
5-(2-ethylbenzyl)-2-furoic acid, m.p. 101°–100° C.;
(±) 5-(1-phenylethyl)-2-furoic acid, m.p. 103°–105° C. (previously made by a different route by Mndzhoyan and Aroyan, Dorklady Acad. Nauk. Armyan, SSR, 1957, 25, 267);
5-(3,4-dimethylbenzyl)-2-fuoric acid, m.p. 131°–133° C.;
5-(2-methylthiobenzyl)-2-furoic acid, m.p. 142°–143° C.;
5-(4-chloro-2-methylbenzyl)-2-furoic acid, m.p. 144°–145° C.;
5-(2-chloro-4-methylbenzyl)-2-furoic acid, m.p. 131.5°–133° C.;
(±) 5-[1-(2-methylphenyl)ethyl]-2-furoic acid, m.p. 116°–117° C. (after crystallization from cyclohexane); (±) 5-(1-phenylpropyl)-2-furoic acid, m.p. 97°–99° C.;
(±) 5-[1-(3-methylphenyl)ethyl]-2-furoic acid, m.p. 98°–100° C.;
(±) 5-[1-(2-chlorophenyl)ethyl]-2-furoic acid, m.p. 80°–86° C.;
(±) 5-[1-(3-chlorophenyl)ethyl]-2-furoic acid, m.p. 95°–98° C.;
(±) 5-[1-(4-chlorophenyl)ethyl]-2furoic acid, m.p. 112°–114° C.;
(±) 5-[1-(2-fluorophenyl)ethyl]-2-furoic acid, m.p. 99°–101° C.;
(±) 5-[1-(2-bromophenyl)ethyl]-2-furoic acid, m.p. 95°–98° C.;
(±) 5-[1-(2,3-dimethylphenyl)ethyl]-2-furoic acid, m.p. 103°–108° C.;
(±) 5-[1-(2,4-dimethylphenyl)ethyl]-2-furoic acid, m.p. 107°–112° C., and
(±) 5-[1-(2,4-dichlorophenyl)ethyl]-2-furoic acid, m.p. 115°–120° C.

e. A warm solution of potassium hydroxide (28 g.) in water (60 ml.) and methanol (120 ml.) was added to a warm solution of methyl 5-(2-methylbenzoyl)-2-furoate [prepared as described in (c) above; 110 g.] in methanol (550 ml.) and the mixture was allowed to stand at ambient temperature for 1 hour. The solution was then basified by the addition of 2N aqueous sodium hydroxide solution (50 ml.) and allowed to stand at ambient temperature overnight. The alkaline solution thus obtained was evaporated to dryness and the residue was dissolved in water. The aqueous solution was magnetically stirred whilst it was made strongly acid by the addition of concentrated hydrochloric acid. The precipitate was collected and washed with water to give 5-(2-methylbenzoyl)-2-furoic acid (100.5 g.), m.p. 155°–157° C.

By proceeding in a similar fashion but replacing the methyl 5-(2-methylbenzoyl)-2-furoate by the appropriate methyl 5-benzoyl-2-furoate prepared as described in (c) above, there were obtained:

5-(2-chlorobenzoyl)-2-furoic acid, m.p. 160°–161° C.;
5-(3-chlorobenzoyl)-2-furoic acid, m.p. 193°–195° C.;
5-(3-methylbenzoyl)-2-furoic acid, m.p. 153°–155° C. (after recrystallisation from toluene);
5-(3,4-dichlorobenzoyl)-2-furoic acid, m.p. 210°–218° C.;
5-(2,3-dimethylbenzoyl)-2-furoic acid, m.p. 195°–197° C. (after recrystallisation from aqueous isopropanol);
5-(2,5-dimethylbenzoyl)-2-furoic acid, m.p. 179°–181° C. (after recrystallisation from aqueous isopropanol);
5-(3,5-dimethylbenzoyl)-2-furoic acid, m.p. 194°–196° C. (after recrystallisation from aqueous isopropanol);
5-(2-bromobenzoyl)-2-furoic acid, m.p. 167°–168° C.;
5(2-ethylbenzoyl)-2-furoic acid, m.p. 133°–135° C., and
5-(4-chloro-2-methyl)-2-furoic acid, m.p. 201°–203° C.

f. 5-(2-Methylbenzoyl)-2-furoic acid [prepared as described in (e) above; 96.6 g.] was added to a solution of potassium hydroxide (70 g.) in diethylene glycol (530 ml.) at 100°–110° C. When the solution was complete, hydrazine hydrate (58%; 53 ml.) was added. The mixture was gradually warmed and then maintained under reflux at 145° C. for 7 hours. Evolution of nitrogen was monitored by collecting the gas over water. Evolution of nitrogen did not completely cease. The reaction mixture was cooled, diluted with water (600 ml.) and stirred while acidifying by dropwise addition of concentrated hydrochloric acid to give crude 5-(2-methylbenzyl)-2-furoic acid in the form of a sticky, brown coloured solid, which was collected, washed with water and dried. The solid thus obtained was dissolved in a mixture of saturated aqueous sodium bicarbonate solution (420 ml.) and water (420 ml.), treated with charcoal and filtered. The filtrate was acidified by the dropwise addition, with stirring, of concentrated hydrochloric acid until the powdery precipitate began to become sticky. The addition of a little 2N aqueous sodium carbonate solution removed this stickiness and a white powdery solid was collected, washed with water and dried to give 5-(2-methylbenzyl)-furoic acid (39 g.), m.p. 136°–138° C., raised to 139°–141° C. by recrystallisation from light petroleum (b.p. 100°–120° C.).

By proceeding in a similar fashion but replacing the 5-(2-methylbenzoyl)-2-furoic acid by the appropriate 5-benzoyl-2-furoic acid prepared as described in (e) above, there were obtained:

5-(2-chlorobenzyl)-2-furoic acid, m.p. 132°–134° C.;
5-(3-chlorobenzyl)-2-furoic acid, m.p. 78°–83° C.;
5-(3-methylbenzyl)-2-furoic acid, m.p. 117°–119° C. (after recrystallisation from aqueous isopropanol);
5-(3,4-dichlorobenzyl)-2-furoic acid, m.p. 138°–140° C.;
5-(2,3-dimethylbenzyl)-2-furoic acid, m.p. 148°–150° C. (after recrystallisation from toluene);
5-(2,5-dimethylbenzyl)-2-furoic acid, m.p. 127°–129° C., and
5-(3,5-dimethylbenzyl-2-furoic acid, m.p. 124°–126° C. (after recrystallisation from aqueous isopropanol). [It is to be observed that, in the reduction of the 5-benzoyl-2-furoic acids with hydrazine hydrate, when a substituent is present in the 2-position of the benzoyl moiety, evolution of nitrogen did not completely cease, while in the case of 5-benzoyl-2-furoic acids without a substituent in the 2-position, evolution of nitrogen ceased after a shorter period, e.g. 1 to 2 hours, and the reaction could be terminated at that point. In the case of the 5-benzyl-2-furoic acids without a substituent in the 2-position, the corresponding 5-benzyl-2-furoic acids were obtained in good yield and in an almost pure state; the yields and purity of 5-benzyl-2-furoic acids with a substituent in the 2-position were usually lower].

g. A mixture of 5-(2-methylbenzyl)-2-furoic acid [prepared as described in (d) or (f) above; 26.2 g.] and cupric oxide (1 g.) was heated at 200° C. for 4 hours until evolution of carbon dioxide almost ceased. The residue was cooled and distilled to give 2-(5-methylbenzyl)furan (16.5 g.), b.p. 118° C./20 mm.Hg, in the form of a pale yellow coloured oil.

By proceeding in a similar fashion, but replacing the 5-(2-methylbenzyl)-2-furoic acid by the appropriate 5-benzyl-2-furoic acid prepared as described in (d) or (f) above, there were obtained:

2-(2-chlorobenzyl)furan, b.p. 65° C./0.06 mm.Hg;
2-(3-chlorobenzyl)furan, b.p. 80°-100° C./0.2 mm.Hg;
2-(2-fluorobenzyl)furan, b.p. 60°-65° C./0.1 mm.Hg;
2-(2-bromobenzyl)furan, b.p. 98°-100° C./0.1 mm.Hg;
2-(2-ethoxybenzyl)furan, b.p. 151°-151.5° C./20 mm.Hg;
2-(3-methylbenzyl)furan, b.p. 126°-128° C./20 mm.Hg;
2-(2,6-dichlorobenzyl)furan, b.p. 120° C./0.2 mm.Hg;
2-(3,4-dichlorobenzyl)furan, b.p. 100° C./0.1 mm.Hg;
2-(2,3-dimethylbenzyl)furan, b.p. 143°-145° C./20 mm.Hg;
2-(2,4-dimethylbenzyl)furan, b.p. 139°-141° C./25 mm.Hg;
2-(2,5-dimethylbenzyl)furan, b.p. 136°-138° C./20 mm.Hg;
2-(3,5-dimethylbenzyl)furan, b.p. 138°-140° C./25 mm.Hg;
2-(2-ethylbenzyl)furan, b.p. 130°-132° C./20 mm.Hg;
($\pm$) 2-(1-phenylethyl)furan, b.p. 119°-121° C./20 mm.Hg;
2-(3,4-dimethylbenzyl)furan, b.p. 140°-142° C./20 mm.Hg;
2-(2-methylthiobenzyl)furan, b.p. 158°-160° C./20 mm.Hg;
2-(4-chloro-2-methylbenzyl)furan, b.p. 155°-160° C./20 mm.Hg;
2-(2-chloro-4-methylbenzyl)furan, b.p. 141°-143° C./20 mm.Hg;
($\pm$) 2-[1-(2-methylphenyl)ethyl]furan, b.p. 122°-125° C./20 mm.Hg;
($\pm$) 2-(1-phenylpropyl)furan, b.p. 118°-120° C./20 mm.Hg;
($\pm$) 2-[1-(3-methylphenyl)ethyl]furan, b.p. 138°-140° C./20 mm.Hg;
($\pm$) 2-[1-(2-chlorophenyl)ethyl]furan, b.p. 122°-128° C./20 mm.Hg;
($\pm$) 2-[1-(3-chlorophenyl)ethyl]furan, b.p. 132°-140° C./20 mm.Hg;
($\pm$) 2-[1-(4-chlorophenyl)ethyl]furan, b.p. 130°-140° C./20 mm.Hg;
($\pm$) 2-[1-(2-fluorophenyl)ethyl]furan, b.p. 108° C./20 mm.Hg;
($\pm$) 2-[1-(2-bromophenyl)ethyl]furan, b.p. 140°-160° C./20 mm.Hg;
($\pm$) 2-[1-(2,3-dimethylphenyl)ethyl]furan, b.p. 144°-150° C./20 mm.Hg;
($\pm$) 2-[1-(2,4-dimethylphenyl)ethyl]furan, b.p. 129°-131° C./20 mm.Hg, and
($\pm$) 2-[1-(2,4-dichlorophenyl)ethyl]furan, b.p. 145°-155° C./20 mm.Hg.

By proceeding in a similar fashion but replacing the 5-(2-methylbenzyl)-2-furoic acid by the appropriate 5-benzoyl-2-furoic acid prepared as described in (e) above there were prepared:

2-(2-chlorobenzoyl)furan, b.p. 130°-140° C./0.2 mm.Hg;
2-(2-bromobenzoyl)furan, b.p. 135°-155° C./0.05 mm.Hg, m.p. 52°-57° C.;
2-(2-ethylbenzoyl)furan, b.p. 162° C./20 mm.Hg;
2-(4-chloro-2-methylbenzoyl)furan, b.p. 132°-144° C./0.05 mm.Hg, m.p. 48°-49° C., and
2-(2-methylbenzoyl)furan, b.p. 152° C./20 mm.Hg.

h. 1-(2-Fluorophenyl)ethyl chloride was prepared as follows:

Thionyl chloride (100 ml.) was added to a solution of 1-(2-fluorophenyl)ethanol [described by McCall, J.A.C.S. 74, 4809 (1952)] (105 g.) in dry chloroform (200 ml.). After the vigorous initial reaction had subsided, the solution was heated at reflux on a steam bath for 30 minutes. The excess of thionyl chloride was removed by repeated co-distillation with dry toluene and the residue was diluted with diethyl ether, washed with water (2 × 100 ml.), dried over sodium sulphate, filtered and evaporated to a yellow liquid, which was distilled to give 1-(2-fluorophenyl)ethyl chloride (73.2 g.), b.p. 70°-75° C./20 mm.Hg, as a pale yellow oil.

By proceeding in a similar manner but replacing 1-(2-fluorophenyl)ethanol by the appropriate phenyl ethanols there were prepared:

1-(2,3-dimethylphenyl)ethyl chloride, as a dark oil which was not distilled;
1-(2,4-dimethylphenyl)ethyl chloride, as a light oil which was not distilled, and
1-(2,4-dichlorophenyl)ethyl chloride, as a light oil which was not distilled.

1-(2,3-Dimethylphenyl)ethanol has been described by Masauda et al. Bull.Jap. Petrol, Inst., 13, 228 (1971).

1-(2,4-Dimethylphenyl)ethanol has been described by Klages, Ber., 35, 2248 (1902).

1-(2,4-Dichlorophenyl)ethanol has been described by Evans et al., J.C.S., 1927, 1164.

i. ($\pm$) 2-($\alpha$-Hydroxybenzyl)furan was prepared as follows:

A solution of furfuraldehyde (288 g.) in diethyl ether (400 ml.) was added over 30 minutes to a stirred solution of phenyl magnesium bromide [prepared from bromobenzene (314 g.) and magnesium (48 g.)] in diethyl ether (1400 ml.) at $-25°$ C. The cooling bath was removed and the mixture was allowed to attain 10° C. over 30 minutes. The mixture was recooled to 0° C. and saturated aqueous ammonium chloride solution was added at that temperature. The mixture was diluted with water (2 liters) and the organic phase was separated. The aqueous phase was filtered and extracted with diethyl ether (3 × 200 ml.) and the combined ethereal solutions were dried over sodium sulphate, filtered and evaporated to dryness. The resulting pale red oil was distilled to give ($\pm$) 2-($\alpha$-hydroxybenzyl)furan (240 g.), b.p. 110°-130° C./0.05 mm.Hg.

By proceeding in a similar manner but replacing bromobenzene by 2-bromotoluene [described by Hübner & Wallach, Zeitschrift fur Chemie (1869) 138], 2-methoxybromobenzene[described by Doran, J.A.C.S. 51, 3449

(1929)], 2-ethylbromobenzene [described by Klouwen & Boelens, Rec. Trav. Chim. 79, 1022 (1960)], 2,3-dichlorobromobenzene (described by Hurtley, J.C.S. 1901, 79, 1302) and 2,5-dichlorobromobenzene [described by Noelting & Kopp, Ber, 38, 3509 (1905)], the following α-hydroxybenzyl furans were prepared:

(±) 2-(α-hydroxy-2-methylbenzyl)furan, b.p. 125°–130° C./0.1 mm.Hg;

(±) 2-(α-hydroxy-2-methoxybenzyl)furan, b.p. 118°–122° C./0.2 mm.Hg;

(±) 2-(2-ethyl-α-hydroxybenzyl)furan, b.p. 110°–112° C./0.15 mm.Hg;

(±) 2-(2,3-dichloro-α-hydroxybenzyl)furan, b.p. 155°–160° C./0.3 mm.Hg, and (±) 2-(2,5-dichloro-α-hydroxybenzyl)furan, b.p. 125°–142° C./0.1 mm.Hg.

j. (±) 2-(2-Chloro-α-hydroxybenzyl)furan was prepared as follows:

Portions of sodium borohydride (total 15 g.) were added over an hour to a stirred solution of 2-(2-chlorobenzoyl)furan (prepared as hereinbefore described; 100 g.) in methanol (500 ml.) at 10°–25° C. After stirring for 1 hour, the solution was heated briefly to the boiling point and, when effervescence had ceased, sodium hydroxide solution (2N, 100 ml.) was added. The solution was heated at reflux for 30 minutes, diluted with water (1 liter) and extracted with diethyl ether (4 × 150 ml.). The combined extracts were washed with water (2 × 100 ml.), dried over sodium sulphate, filtered and evaporated to a clear oil, which was distilled to give (±) 2-(2-chloro-α-hydroxybenzyl)furan (71 g.), b.p. 136° C./0.1 mm.Hg, as a viscous yellow oil.

By proceeding in a similar fashion but replacing 2-(2-chlorobenzoyl)furan by 2-(2-bromobenzoyl)furan (prepared as hereinbefore described), there was prepared:

(±) 2-(2-bromo-α-hydroxybenzyl)furan, b.p. 130°–140° C./0.05 mm.Hg.

k. (±) 2-(2-Chloro-α-methoxybenzyl)furan was prepared as follows:

A soluton of (±) 2-(2-chloro-α-hydroxybenzyl)furan [prepared as described in (j) above] (31.3 g.) in dimethylformamide (100 ml.) was treated with sodium hydride (4.1 g.) with ice cooling. Methyl iodide (28.4 g.) was added to the stirred solution over 15 minutes at 15°–30° C. with ice cooling and the mixture was allowed to stand at ambient temperature for 1 hour. The mixture was then diluted with diethyl ether (300 ml.) and filtered. The filtrate was washed with water (3 × 500 ml.), dried over sodium sulphate and evaporated to give a light red oil, which was distilled to give (±) 2-(2-chloro-α-methoxybenzyl)furan (30 g.), b.p. 115° C./0.1 mm.Hg.

By proceeding in a similar fashion but replacing the (±) 2-(2-chloro-α-hydroxybenzyl)furan by the appropriate (±) 2-(α-hydroxybenzyl)furans indicated below, and prepared as described in (i) and (j) above, there were prepared:

(±) 2-(α-methoxybenzyl)furan, b.p. 76° C./0.05 mm.Hg, from (±) 2-(α-hydroxybenzyl)furan, (±) 2-(2-bromo-α-methoxybenzyl)furan, b.p. 90°–100° C./0.05 mm.Hg, from (±) 2-(2-bromo-α-hydroxybenzyl)furan, (±) 2-(2-methyl-α-methoxybenzyl)furan, b.p. 100° C./0.1 mm.Hg, from (±) 2-(α-hydroxy-2-methylbenzyl)furan, and (±) 2-(2-ethyl-α-methoxybenzyl)furan, b.p. 97°–98° C./0.35 mm.Hg, from (±) 2-(2-ethyl-α-hydroxybenzyl)furan.

By proceeding in a similar fashion but replacing the (±) 2-(2-chloro-α-hydroxybenzyl)furan by (±) 2-(α-hydroxybenzyl)furan and the methyl iodide by ethyl iodide, there was obtained (±) 2-(α-ethoxybenzyl)furan, b.p. 89°–92° C./0.15 mm.Hg.

l. (±) 2-[1-(2-Methoxyphenyl)ethyl]furan was prepared as follows:

Sodium metal (44.1 g.) was added at reflux over 45 minutes to a solution of (±) 1-(2-furyl)-1-(2-methoxyphenyl)ethanol (43.6 g.) in ethanol (560 ml.). The mixture was heated at reflux for 45 minutes, when more sodium (21.8 g.) was added in portions. Heating was continued until the sodium had dissolved and the excess of ethanol was removed by evaporation.

Ice water (600 ml.) was added to the residue and the mixture was steam distilled. The distillate was extracted with diethyl ether (3 × 400 ml.). The combined extracts were dried over sodium sulphate and evaporated to give a yellow oil. Distillation of this oil gave (±) 2-[1-(2-methoxyphenyl)ethyl]furan (22.5 g.), b.p. 133°–138° C./20 mm.Hg, in the form of a colourless oil.

By proceeding in a similar fashion but replacing (±) 1-(2-methoxyphenyl)-1-(2-furyl)ethanol by (±) 2-(α-hydroxy-2-isopropylbenzyl)furan, there was obtained 2-(2-isopropylbenzyl)furan, b.p. 136°–138° C./15 mm.Hg.

(±)1-(2-Furyl)-1-(2-methoxyphenyl)ethanol (b.p. 115°–118° C./0.15 mm.Hg; m.p. 64°–66° C.) was prepared by the procedure hereinbefore described in (i) for the preparation of (±) 2-α-hydroxybenzylfuran but replacing the furfuraldehyde by 2-acetylfuran [described by Levine et al, J.A.C.S. 71, 1208,(1949)] and the bromobenzene by 2-methoxybromobenzene.

(±) 2-(α-Hydroxy-2-isopropylbenzyl)furan (b.p. 110° C./0.15 mm.Hg) was prepared by the procedure hereinbefore described in (i) for the preparation of (±) 2-α-hydroxybenzylfuran but replacing the bromobenzene by 2-isopropylbromobenzene (described by Crawford and Stuart, J.C.S., 1952, 4445).

m. (±) 2-[1-(2-Ethylphenyl)ethyl]furan was prepared as follows:

A solution of 1-(2-ethylphenyl)-1-(2-furyl)ethylene (27 g.) in ethanol (150 ml.) in the presence of 10% palladium on charcoal (0.5 g.) was treated with hydrogen at room temperature for 3 hours. The mixture was filtered and evaporated to give a clear oil which was distilled to give (±) 2-[1-(2-ethylphenyl)ethyl]-furan (23.9 g.), b.p. 130°–150° C./20 mm.Hg, in the form of a yellow oil.

By proceeding in a similar fashion but replacing 1-(2-ethylphenyl)-1-(2-furyl)ethylene by 1-(4-chloro-2-methylphenyl)-1-(2-furyl)ethylene and 1-(2-methylphenyl)-1-(2-furyl)-prop-1-ene, respectively, there were obtained: (±) 2-[1-(4-chloro-2-methylphenyl)ethyl]furan, b.p. 144°–162° C./10 mm.Hg, and (±) 2-[1-(2-methylphenyl)propyl]furan, b.p. 125°–130° C./20 mm.Hg.

1-(2-Ethylphenyl)-1-(2-furyl)ethylene was prepared as follows:

2-(2-Ethylbenzoyl)furan [prepared as described in (i) above] (48 g.) in diethyl ether (150 ml.) was added to a stirred solution of methyl magnesium iodide [prepared from methyl iodide (34.1 g.) and magnesium (5.8 g.)] in diethyl ether (50 ml.) at 0°–10° C. The mixture was stirred for 1 hour without cooling.

Saturated aqueous ammonium chloride solution (125 ml.) was added over 20 minutes at 0° C. and the mixture was stirred for 10 minutes and filtered. The ethereal layer was washed with water (2 × 100 ml.), dried over sodium sulphate, filtered and evaporated to give a viscous red oil, which was distilled. As a result of dehydration during the distillation, 1-(2-ethylphenyl)-1-(2-furyl)ethylene (29.3 g.), b.p. 110° C./0.1 mm.Hg, was obtained in the form of a yellow oil.

By proceeding in a similar fashion but replacing 2-(2-ethylbenzoyl)furan by 2-(4-chloro-2-methylbenzoyl)furan [prepared as described in (i) above], there was obtained:

1-(4-chloro-2-methylphenyl)-1-(2-furyl)ethylene, b.p. 116°-130° C./0.5 mm.Hg.

By proceeding in a similar fashion but replacing methyl iodide by ethyl iodide and 2-(2-ethylbenzoyl)furan by 2-(2-methylbenzoyl)furan [prepared as described in (i) above], there was obtained:

1-(2-methylphenyl)-1-(2-furyl)-prop-1-ene, b.p. 120°-125° C./0.1 mm.Hg.

EXAMPLE 4

(±) 3-(2-Chloro-α-hydroxy)benzylpyridazine (prepared as described in Example 3) (4.7 g.) was suspended with magnetic stirring in an aqueous buffer solution prepared by dissolving sodium dihydrogen phosphate (1.6 g.) in a saturated aqueous solution of magnesium sulphate (50 ml.). The suspension was heated to 50° C. and potassium permanganate (3 g.) was added in portions over 2 hours at 45°-50° C. The suspension was filtered and the filtrate and filter pad were extracted with chloroform (5 × 100 ml.). The combined extracts were washed with water (2 × 100 ml.), dried over sodium sulphate and evaporated to give a white solid, which was crystallised from cyclohexane (300 ml.) to give 3-(2-chlorobenzoyl)pyridazine (2.6 g.), m.p. 105°-107° C, in the form of colourless needles.

By proceeding in a similar fashion but replacing the (±) 3-(2-chloro-α-hydroxybenzyl)pyridazine by the appropriate (±) 3-(α-hydroxybenzyl)pyridazines indicated below and prepared as described in Example 3, there were prepared:

3-(2-methylbenzoyl)pyridazine, m.p. 73°-74° C., from (±) 3-(α-hydroxy-2-methylbenzyl)pryidazine,
3-(2-ethylbenzoyl)pyridazine, m.p. 53.5°-55° C., from (±) 3-(2-ethyl-α-hydroxybenzyl)pyridazine,
3-(2-bromobenzoyl)pyridazine, m.p. 88°-90° C., from (±) 3-(2-bromo-α-hydroxybenzyl)pyridazine,
3-(2,3-dichlorobenzoyl)pyridazine, m.p. 92°-93° C., from (±) 3-(2,3-dichloro-α-hydroxybenzyl)pyridazine,
3-(2,5-dichlorobenzoyl)pyridazine, m.p. 69°-71° C., from (±) 3-(2,5-dichloro-α-hydroxybenzyl)pyridazine, and 3-benzoylpyridazine, m.p. 70°-71° C. (after recrystallisation from toluene/n-hexane) from (±) 3-α-hydroxybenzylpyridazine.

EXAMPLE 5

A solution of 3-benzoylpyridazine (prepared as described in Example 4) (3.7 g.) in ethanol (20 ml.) was mixed with a solution of hydroxylamine hydrochloride (3.5 g.) and sodium acetate (6 g.) in water (12 ml.) and heated for 1 hour on a steam bath. On cooling, white crystals were deposited, which were filtered off and recrystallised from ethyl acetate (200 ml.) to give 3-benzyl-α-hydroxyiminopyridazine (Form A) (1.5 g.), m.p. 200°-202° C., having the structural configuration:

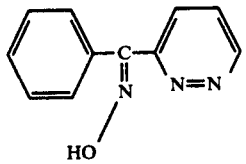

(A)

, in the form of fine white crystals.

Dilution of the mother liquors with n-hexane (200 ml.) gave 3-benzyl-α-hydroxyiminopyridazine (Form B) (1.0 g.), m.p. 163°-165° C., having the structural configuration:

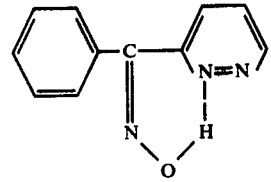

(B)

, in the form of fine pink needles.

By proceeding in a similar fashion but replacing the 3-benzoylpyridazine by 3-(2-methylbenzoyl)pyridazine (prepared as described in Example 4), 3-(2-methyl-α-hydroxyiminobenzyl)pyridazine, m.p. 184°-186° C., was obtained as a single isomer having the structural configuration:

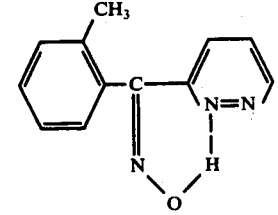

(B)

EXAMPLE 6

A solution of sodium methoxide was prepared by the addition of sodium hydride (0.72 g.) to methanol (25 ml.). (±) 3-α-Chlorobenzylpyridazine (prepared as described in Example 2) (4.1 g.) was heated at reflux in this solution for 2 hours and the mixture was evaporated to dryness. The residue was dissolved in a mixture of diethyl ether and water and the ethereal layer was separated, dried over sodium sulphate and evaporated to give a brown oil. Distillation of this oil gave (±) 3-α-methoxybenzylpyridazine (1.8 g.), b.p. 140°-180° C./0.2-0.4 mm.Hg.

EXAMPLE 7

By proceeding in a manner similar to that described in Example 3 but replacing the 2-(2-methylbenzyl)furan by (±) 2-(α,2-dimethoxybenzyl)furan, there was obtained (±) 3-(α,2-dimethoxybenzyl)pyridazine, m.p. 110°-111° C.

(±) 2-(α,2-Dimethoxybenzyl)furan (b.p. 112°-115° C./0.1 mm.Hg) was prepared in a manner similar to that described in Example 3(k) for the preparation of (±) 2-(2-chloro-α-methoxybenzyl)furan but replacing the (±) 2-(2-chloro-α-hydroxybenzyl)furan by (±) 2(α-hydroxy-2-methoxybenzyl)furan.

(±) 2-(α-Hydroxy-2-methoxybenzyl)furan was prepared as described in Example 3(i).

EXAMPLE 8

By proceeding in a manner similar to that described in Example 3 but replacing the 2-(2-methylbenzyl)furan by (±) 2-[1-(2,3-dichlorophenyl)ethyl]furan, there was obtained (±) 3-[1-(2,3-dichlorophenyl)ethyl]pyridazine, m.p. 96°–98° C.

(±) 2-[1-(2,3Dichlorophenyl)ethyl]furan (b.p. 108°–112° C./0.3 mm.Hg) was prepared in a manner similar to that described in Example 3(m) for the preparation of (±) 2-[1-(2-ethylphenyl)ethyl]furan but replacing the 1-(2-ethylphenyl)-1-(2-furyl)ethylene by 1(2,3-dichlorophenyl)-1-(2-furyl)ethylene.

1-(2,3-Dichlorophenyl)-1-(2-furyl)ethylene was prepared as follows:

(±) 1-(2,3-Dichlorophenyl)-1-(2-furyl)ethanol (92 g.) was heated on a steam bath in pyridine (250 ml.) containing p-toluenesulphonyl chloride (69 g.) for 1 hour. The solution was poured into ice water (1 liter) and extracted with diethyl ether (5 × 500 ml.). The combined ethereal extracts were washed with water (2 × 500 ml.), dried over sodium sulphate, filtered and evaporated to give a dark oil, which was distilled to give 1-(2,3-dichlorophenyl)-1-(2-furyl)ethylene as a pale yellow liquid (46 g.), b.p. 140°–180° C./20 mm.Hg.

The undistilled (±) 1-(2,3-dichlorophenyl)1-(2-furyl)ethanol employed above was obtained as described in Example 3(i) for the preparation of (±) 2-α-hydroxybenzylfuran but by replacing the furfuraldehyde by acetylfuran and the bromobenzene by 2,3-dichlorobromobenzene.

EXAMPLE 9

By proceeding in a manner similar to that described in Example 4 for the preparation of 3-(2-chlorobenzoyl)pyridazine but replacing the (±) 3-(2-chloro-α-hydroxy)benzylpyridazine by the appropriate quantity of (±) 3-(α-hydroxy-2-methoxybenzyl)pyridazine (prepared as described in Example 3), there was obtained 3-(2-methoxybenzoyl)pyridazine, m.p. 125°–126° C. (after crystallisation from aqueous ethanol).

EXAMPLE 10

(±) 1-(2-Furyl)-1-phenylethanol (43 g.) was dissolved in a solution of hydrazine hydrate (25 ml.) in ethanol (100 ml.). Formic acid (23 ml.) was added to the solution cautiously in portions and the heterogeneous mixture was heated at reflux on a steam bath for 4 hours. After 1 hour the mixture became homogeneous. The solution was evaporated to low volume and the residue was digested with a mixture of diethyl ether (100 ml.) and water (200 ml.). Dilute sodium hydroxide solution was added to adjust the pH to 9 and the ether layer was separated. The aqueous layer was extracted with diethyl ether (2 × 150 ml.) and the combined ethereal extracts were washed with water (3 × 150 ml.) and filtered. The filtrate was extracted with 2N hydrochloric acid (5 × 100 ml.). The combined acidic extracts were washed with diethyl ether (2 × 200 ml.) and basified by the addition of 50% aqueous sodium hydroxide solution. The oil which was deposited was extracted with diethyl ether (2 × 200 ml.) and the combined extracts were washed with water (2 × 200 ml.), dried over sodium sulphate, filtered and evaporated to give a brown oil, which was distilled to give 3-(1-phenylethyl)pyridazine (5.4 g.), m.p. 43°–48° C. (b.p. 120° C./0.05 mm.Hg), as an off-white solid.

By proceeding in a similar manner but by replacing the (±) 1-(2-furyl)-1-phenylethanol by the appropriate quantity of 2-α-hydroxybenzylfuran [prepared as described in Example 3(i)] or (±) 2-(α-hydroxy-2-methylbenzyl)furan [prepared as described in Example 3(i)], there were obtained 3-benzylpyridazine, m.p. 60°–62° C., and 3-(2-methylbenzyl)pyridazine, m.p. 83°–85° C., respectively.

The undistilled 1-(2-furyl)-1-phenylethanol employed above was obtained in a manner similar to that described for the preparation of (±) 2-(α-hydroxybenzyl)furan in Example 3(i) but replacing the furfuraldehyde by the appropriate quantity of acetyl furan.

EXAMPLE 11

A solution of 3-(1-cyano-1-phenylethyl)-pyridazine (1 g.) in ethylene glycol (10 ml.) and water (1 ml.) containing potassium hydroxide (0.3 g.) was heated at reflux for 6 hours. The yellow solution was diluted with water (40 ml.) and extracted with chloroform (3 × 25 ml.), dried over magnesium sulphate, filtered and evaporated to give a cream-coloured solid (0.8 g.). 3-(1-Phenylethyl)-pyridazine (0.5 g.), m.p. 44°–45° C., was obtained from the cream-coloured solid in the form of colourless crystals by recrystallisation from cyclohexane.

The 3-(1-cyano-1-phenylethyl)pyridazine employed above was prepared in the following manner:

A solution of 3-chloro-6-(1-cyano-1-phenyl)-ethylpyridazine (15.3 g.) in ethanol (155 ml.) containing aqueous ammonium hydroxide solution (s.g. 0.880; 17 ml.) was treated with hydrogen in the presence of palladium on charcoal (5% Pd) at ambient temperature and normal atmospheric pressure for 5 hours.

After filtration, the filtrate was evaporated to dryness and the residue extracted with chloroform (3 × 70 ml.). The combined extracts were washed with water (2 × 50 ml.), dried over magnesium sulphate and evaporated to dryness. The light brown solid thus obtained was recrystallised from a mixture of cyclohexane (650 ml.) and ethanol (30 ml.) to give 3-(1-cyano-1-phenylethyl)-pyridazine (9.5 g.), m.p. 113.5°–115° C.

The 3-chloro-6-(1-cyano-1-phenylethyl)pyridazine employed above was prepared in the following manner:

Triethyl benzyl ammonium chloride (0.25 g.) was added to a well stirred mixture of 2-phenyl propionitrile (7.2 g.) [prepared as described by a Hauser & Brasen, J.A.C.S. 78, 494 (1956], 3,6-dichloropyridazine (7.45 g.) [prepared as described by Jackiewiez et al, Acta. Polon. Pharm. 17, 355 (1960)] and 50% aqueous sodium hydroxide solution (7.5 ml.). After stirring for 30 minutes, a further quantity of triethyl benzyl ammonium chloride (0.2 g.) was added and the temperature of the mixture rose to 77° C. The viscous mixture was stirred for 4 hours until ambient temperature had been regained, when it was diluted with chloroform (150 ml.). The solution thus obtained was washed with water (4 × 50 ml.), dried over magnesium sulphate, filtered and evaporated to give a brown gum. Repeated crystallisation of the gum from cyclohexane gave 3-chloro-6-(1-cyano-1-phenylethyl)pyridazine (5.2 g.), m.p. 116.5°–117.5° C., as a light brown solid.

According to a further feature of the present invention, there are provided compositions suitable for herbicidal use comprising one or more of the pyridazine derivatives of general formula I in association with, and preferably homogenously dispersed in, one or more compatible herbicidally-acceptable diluents or carriers (i.e. diluents or carriers of the type generally accepted in the art as being suitable for use in herbicidal compositions and which are compatible with compounds of general formula I). The term "homogeneously dispersed" is used to include compositions in which the compounds of general formula I are dissolved in the other components. The term "herbicidal compositions" is used in a broad sense to include not only compositions which are ready for use as herbicides but also concentrates which must be diluted before use. Preferably, the compositions contain from 0.05 to 90% by weight of compounds of general formula I.

The herbicidal compositions may contain both a diluent or carrier and a surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates. Examples of suitable solid diluents or carriers are aluminium silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the compounds of general formula I with solid diluents or by impregnating the solid diluents or carriers with solutions of the compounds of general formula I in volatile solvents, evaporating the solvents and, if necessary, grinding the products so as to obtain powders. Granular formulations may be prepared by absorbing the compounds of general formula I (dissolved in volatile solvents) onto the solid diluents or carriers in granular form and evaporating the solvents, or by granulating compositions in powder form obtained as described above. Solid herbicidal compositions, particularly wettable powders, may contain wetting or dispersing agents (for example of the types described above), which may also, when solid, serve as diluents or carriers.

Liquid compositions according to the invention may take the form of aqueous, organic or aqueous-organic solutions, suspensions, and emulsions which may incorporate a surface-active agent. Suitable liquid diluents for incorporation in the liquid compositions include water, acetophenone, cyclohexanone, isophorone, toluene, xylene and mineral, animal and vegetable oils (and mixtures of these diluents). Surface-active agents, which may be present in the liquid compositions, may be ionic or non-ionic (for example of the types described above) and may, when liquid, also serve as diluents or carriers. Wettable powders and liquid compositions in the form of concentrates may be diluted with water or other suitable diluents, for example mineral or vegetable oils, particularly in the case of liquid concentrates in which the diluent or carrier is an oil, to give compositions ready for use. When desired, liquid compositions of the compounds of general formula I may be used in the form of self-emulsifying concentrates containing the active substances dissolved in the emulsifying agents or in solvents containing emulsifying agents compatible with the active substances, the simple addition of water to such concentrates producing compositions ready for use.

Herbicidal compositions according to the present invention may also contain, if desired, conventional adjuvants such as adhesives, colouring agents and corrosion inhibitors. These adjuvants may also serve as carriers or diluents.

Herbicidal compositions according to the present invention may also comprise the compounds of general formula I in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example phenoxyalkanoic acids [e.g. 4-(4-chloro-2-methylphenoxy)-butyric acid, 4-(2,4-dichlorophenoxy)-butyric acid, 2-(4-chloro-2-methylphenoxy)-propionic acid, 2-(2,4-dichlorophenoxy)-propionic acid, 4-chloro-2-methylphenoxyacetic acid, 2,4-dichlorophenoxyacetic acid and 2,4,5-trichlorophenoxyacetic acid], benzoic acid derivatives (e.g. 2,3,6-trichlorobenzoic acid, 2-methoxy-3,6-dichlorobenzoic acid and 3-amino-2,5-dichlorobenzoic acid), halogenated aliphatic acids (e.g. trichloroacetic acid and 2,2-dichloropropionic acid), carbamates [e.g. isopropyl N-(3-chlorophenyl)-carbamate, isopropyl N-phenylcarbamate, and 3-chloro-2-butynyl N-(3-chlorophenyl)-carbamate], thiocarbamates (e.g. S-2,3,3-trichlorallyl N,N-diisopropylthiocarbamate and S-propyl N,N-dipropylthiocarbamate), amides [e.g. 3,4-dichloropropionanilide, 2-chloro-N-isopropylacetanilide and D-N-ethyl-2-(phenylcarbamoyloxy)-propionamide], urea derivatives [e.g. N'-(4-chlorophenyl)-N,N-dimethylurea, N,N-dimethyl-N'-phenylurea, N'-(3,4-dichlorophenyl)-N,N-dimethylurea and N'-(4-chlorophenyl)-N-methoxy-N-methylurea], diazines, (e.g. 5-bromo-3-isopropyl-6-methyl-uracil and 3-cyclohexyl-5,6-trimethylene-uracil), triazines (e.g. 2-chloro-4,6-bisethylamino-1,3,5-triazine, 2-chloro-4-ethylamino-6-isopropylamino-1,3,5-triazine and 6-(3-methoxypropylamino)-4isopropylamino-2-methylthio-1,3,5-triazine), substituted phenols [e.g. 2-methyl-4,6-dinitrophenol, 2-(1-methyl-propyl)-4,6-dinitrophenol and 2,4-dichlorophenyl 4-nitrophenyl ether], quaternary ammonium derivatives (e.g. 1,1'-ethylene-2,2'-bipyridylium and 1,1-dimethyl-4,4'-dipyridylium salts), benzonitrile derivatives (e.g. 2,6-dichlorobenzonitrile and 3,5-diiodo- and 3,5-dibromo-4-hydroxybenzonitriles and their salts and esters e.g. their octanoates), triazole derivatives (e.g. 3-amino-1,2,4-triazole), thiocarbonyl derivatives [e.g. di(methoxythiocarbonyl)disulphide], benzenesulphonylcarbamates (e.g. methyl 4-aminobenzenesulphonylcarbamate, methyl 4-nitrobenzenesulphonylcarbamate and methyl 4-methoxycarbonylaminobenzenesulphonylcarbamate), 4-chloro-2-oxo-benzothiazolin-3-ylacetic acid, 2-t-butyl-4-(2,4-dichloro-5-isopropoxyphenyl)-5-oxo-1,3,4-oxadiazole, and 2,6-dinitro-N,N-dipropyl-4-trifluoromethylaniline, insecticides, e.g. naphth-1-yl N-methylcarbamate, and fungicides, e.g. 2,6-dimethyl-4-tridecylmorpholine, methylN-(1-butylcarbamoylbenzimidazol- 2-yl)-carbamate and 1,2-bis-(3-methoxycarbonyl-2-thioureido)benzene. Other biologically active materials which may be included in, or used in conjunction with, the herbicidal compositions of the present invention are plant growth regulators, e.g. maleic hydrazide, N-dimethylaminosuccinamic acid, (2-chloroethyl)trimethylammonium chloride and 2-chloroethane phosphonic acid, or fertilizers, e.g. containing nitrogen, potassium and phosphorus and trace elements known to be essential to successful plant life, e.g. iron, magnesium, zinc, manganese, cobalt and copper.

According to a further feature of the present invention there is provided an article of manufacture comprising at least one of the pyridazine derivatives of general formula I or, as is preferred, a herbicidal composition as hereinbefore described, and preferably a herbicidal concentrate which must be diluted before use, comprising at least one of the pyridazine derivatives of general formula I within a container for the aforesaid derivative or derivatives of general formula I, or a said herbicidal composition, and instructions physically associated with the aforesaid container setting out the manner in which the aforesaid derivative or derivatives of general formula I or herbicidal composition contained therein is to be used to control the growth of weeds. The containers will normally be of the types conventionally used for the storage of chemical substances which are solids at normal ambient temperatures and herbicidal compositions, particularly in the form of concentrates, for example cans and drums of metal, which may be internally-lacquered, and plastics materials, bottles of glass and plastics materials and, when the contents of the container is a solid, for example granular herbicidal compositions, boxes, for example of cardboard, plastics materials and metal, or sacks. The containers will normally be of sufficient capacity to contain amounts of the pyridazine derivatives or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between ¼ kg. and 8 kg. of active material per hectare in the manner and for the purposes hereinbefore described.

The following Examples illustrate the herbicidal compositions of the present invention.

EXAMPLE 12

A wettable powder is formed from:

| | |
|---|---|
| 3-(2-methylbenzyl)pyridazine | 25% w/w |
| Ethylan CP (an octylphenol-polyglycol ether containing 9 glycol units) | 2.5% w/w |
| Celite PG (synthetic magnesium silicate) | 72.5% w/w | by dissolving the Ethylan CP in the minimum volume of acetone and adding the solution to the Celite PF in a blender. After the acetone has evaporated, the solid pyridazine derivative is added, blended in and the product milled. The wettable powder thus obtained may be suspended in water and applied at a rate of 1 kg. of pyridazine derivative in 200 liters of spray fluid per hectare (a) to an emerged crop of oil seed rape to control the growth of *Alopecurus myosuroides*, *Poa* spp., volunteer barley and *Polygonum* spp. by post-emergence application or (b) to a crop-growing area sown with oil seed rape to control the growth of *Alopecurus myosuroides*, *Poa annua*, *Lolium perenne*, *Apera spicaventi*, *Stellaria media*, *Papaver rhoeas* and *Veronica persica* by pre-emergence application to the soil surface before weed and crop emergence.

Similar wettable powders may be obtained by replacing the 3-(2-methylbenzyl)pyridazine by any other solid pyridazine derivative of general formula I, in particular a compound of general formula I wherein $R^1$ represents a fluorine, chlorine, bromine or iodine atom or a methyl, ethyl, methoxy or ethoxy group, $R^2$, $R^3$ and $R^4$ each represent a hydrogen atom, and $n$ represents zero or an integer from 1 to 5 inclusive.

The wettable powder may be placed in a suitable container, e.g. a cardboard box, in an amount sufficient for the treatment of 1 hectare of the rape-growing area, i.e. 4 kg. of wettable powder containing 1 kg. of 3-(2-methylbenzyl)pyridazine, with associated instructions for use corresponding to the indications set out immediately above, the instructions being preferably printed on the container or on a label or tag affixed to the container.

EXAMPLE 13

A self-emulsifying concentrate is formed from:

| | |
|---|---|
| 3-(2-bromobenzyl)pyridazine | 15% w/v |
| Duoterics MB1/MB2 (an anionic/nonionic surface-active blend containing calcium alkyl aryl sulphonates) | 10% w/v |
| a mixture of cyclohexanone and Aromasol 'H' (an aromatic solvent consisting predominantly of isomeric trimethylbenzenes) (3:1) | to 100% by volume | by dissolving the pyridazine derivative in a portion of the mixture of cyclohexanone and Aromasol 'H', then adding, with stirring, the Duoterics MB1/MB2 and then adding, with stirring, the remainder of the mixture of cyclohexanone and Aromasol 'H'. The self-emulsifying liquid thus obtained may be diluted with water and applied at a rate of 1 kg. of pyridazine derivative in 200 liters of spray fluid per hectare to a crop-growing area planted with soya bean to control the germination and growth of pigweeds, fathen, *Eleusine* spp., crabgrass and barnyard grass by application to the soil before emergence of both crop and weeds.

EXAMPLE 14

Granules are formed from:

| | |
|---|---|
| 3-(2-chlorobenzyl)pyridazine | 10% w/w |
| Waxoline Red OS (4-ortho-tolylazo-orthotoluidine-2-naphthol dye) | 0.2% w/w |
| Attapulgite granules [sorptive silica clay, AA grade or hardness; RVM/regular volatile matter grade] | to 100% by weight | by dissolving the pyridazine derivative and the Waxoline Red OS in the minimum quantity of acetone, then spraying or dripping the acetone solution onto the granules and allowing the acetone to evaporate with constant stirring. The granules thus obtained may be applied to the soil at a rate of 20 kg., i.e. 2 kg. of pyridazine derivative, per hectare, with shallow incorporation, to a crop-growing area to be used for growing a crop of dwarf beans before the beans are sown, to control the germination and growth of fathen, pigweeds, *Polygonum* spp., foxtails and crabgrass.

EXAMPLE 15

A self-emulsifying concentrate is formed by the procedure described in Example 13 but replacing the 3-(2-bromobenzyl)pyridazine by 3-(2-ethylbenzyl)-pyridazine (20% w/v). The self-emulsifying liquid thus obtained may be diluted with water and applied at a rate of 1 kg. of pyridazine derivatives in 300 liters of spray fluid per hectare to a crop-growing area to be planted with sugar beet and incorporated into the soil before the crop is sown to control the germination and growth of *Avena fatua, Alopecurus myosuroides, Digitaria sanguinalis, Echinochloa crus-galli, Setaria viridis, Eleusine indica* and *Amaranthus retroflexus*.

Similar self-emulsifying concentrates may be obtained by replacing the 3-(2-ethylbenzyl)pryidazine by a compound of general formula I wherein $R^1$ represents a fluorine, chlorine, bromine or iodine atom or methyl, ethyl, methoxy or ethoxy group, $R^2$, $R^3$ and $R^4$ each represent a hydrogen atom, and $n$ represents zero or an integer from 1 to 5 inclusive.

EXAMPLE 16

A water-soluble concentrate is formed from:

| | |
|---|---|
| 3-(2-methoxybenzyl)pyridazine | 20% w/v |
| Ethylan KEO (a nonylphenyl ethylene oxide condensate containing 9.5 moles of ethylene oxide) | 10% w/v |
| dimethylformamide | to 100% by volume | by dissolving the pyridazine derivative in a portion of the dimethylformamide, stirring in the Ethylan KEO and then adding the remainder of the dimethylformamide. The water soluble concentrate thus obtained may be dissolved in water and applied at a rate of 1 kg. of pyridazine derivative in 400 liters of spray fluid per hectare to a crop-growing area planted with wheat to control *Avena fatua, Alopecurus, myosuroides, Lolium perenne, Apera spica-venti, Poa annua, Stellaria media, Galium aparine, Matricaria inodora, Papaver rhoeas* and *Veronica persica* by application to the soil after sowing of the crop and before the emergence of the weeds and crop.

Similar water-soluble concentrates may be obtained by replacing the 3-(2-methoxybenzyl)pyridazine by a compound of general formula I wherein $R^1$ represents a fluorine, chlorine, bromine or iodine atom or a methyl, ethyl, methoxy or ethoxy group, $R^2$, $R^3$ and $R^4$ each represents a hydrogen atom, and $n$ represents zero or an integer from 1 to 5 inclusive.

EXAMPLE 17

Granules are formed by the procedure described in Example 14 but replacing the 3-(2-chlorobenzyl)pyridazine by 3-(2,4-dimethylbenzyl)pyridazine. The granules thus obtained may be applied to the soil of a crop-growing area to be sown with maize at a rate of 20 kg., i.e. 2 kg. of pyridazine derivative, per hectare, with shallow incorporation into the soil, to control the germination and growth of *Digitaria sanguinalis, Echinochloa crusqalli, Eleusine indica, Paspalum dilatatum, Setaria* spp. and *Amaranthus retroflexus*.

Similar granules may be obtained by replacing the 3-(2,4-dimethylbenzyl)pyridazine by a compound of general formula I wherein $R^1$ represents a fluorine, chlorine, bromine or iodine atom or a methyl, ethyl, methoxy or ethoxy group, $R^2$, $R^3$ and $R^4$ each represent a hydrogen atom, and $n$ represents zero or an integer from 1 to 5 inclusive.

EXAMPLE 18

A self-emulsifying concentrate is formed from:

| | |
|---|---|
| 3-(1-phenylethyl)pyridazine | 20% w/v |
| Duoterics MB1/MB2 | 10% w/v |
| Aromasol 'H' | to 100% by volume | by dissolving the pyridazine derivative in a portion of the Aromasol 'H', then adding, with stirring, the Duoterics MB1/MB2 and then adding, with stirring, the remainder of the Aromasol 'H'. The self-emulsifying liquid thus obtained may be diluted with water and applied at a rate of 1.5 kg . of pyridazine derivative in 300 liters of spray fluid per hectare to a crop-growing area containing an emerged crop of dwarf beans to control the germination and growth of *Avena fatua, Stellaria media, Alopecurus myosuroides, Poa annua, Polygonum lapathiofolium* and *Galium aparine* by application to the soil before weed emergence.

Similar self-emulsifying concentrates may be obtained by replacing the 3-(1-phenylethyl)pyridazine by a compound of general formula I wherein $R^1$ represents a fluorine, chlorine, bromine or iodine atom or a methyl, ethyl, methoxy or ethoxy group, $R^2$ represents a methyl group, $R^3$ and $R^4$ each represent a hydrogen atom, and $n$ represents zero or an integer from 1 to 5 inclusive.

EXAMPLE 19

A wettable powder is formed by the procedure described in Example 12 but replacing the 3-(2-methylbenzyl)pyridazine by 3-[1-(2-methylphenyl)ethyl]pyridazine (50% w/w) and utilizing Ethylan CP (2.5% w/w) and Celite PF (47.5% w/w). The wettable powder thus obtained may be suspended in water and applied (a) at a rate of 3 kg. of pyridazine derivative in 300 liters of spray fluid per hectare in a crop of sugar cane as a directed spray, i.e. avoiding application to the sugarcane, to control the growth of emerged seedling weeds and to prevent the germination and growth of weeds not yet emerged, in particular *Digitaria sanguinalis, Eleusine indica, Echinochloa crus-galli, Paspalum dilatatum, Sorghum halepense, Cyperus rotundus, Portulaca oleracea* and *Amaranthus retroflexus*, or (b) at a rate of 2 kg. of pyridazine derivative in 200 liters of spray fluid per hectare to an area of stubble left after the harvesting of a crop in the autumn and thoroughly and deeply incorporated into the soil by rotovation to control the growth of couch grasses, e.g. *Agropyron repens, Argrostis, gigantea, Agrostis stolonifera* and *Holcus mollis*. Crops of potatoes may then be sown in the same crop-growing area the following spring.

Similar wettable powders may be obtained by replacing the 3-[1-(2-methylphenyl)ethyl]pyridazine by a compound of general formula I wherein $R^1$ represents of fluorine, chlorine, bromine or iodine atom or a methyl, ethyl, methoxy or ethoxy group, $R^2$ represents a methyl group, $R^3$ and $R^4$ each represent a hydrogen atom, and $n$ represents zero or an integer from 1 to 5 inclusive.

EXAMPLE 20

A self-emulsifying concentrate is formed by the procedure described in Example 13 but replacing the 3-(2-bromobenzyl)pyridazine by 3-[1-(2-ethylphenyl)-ethyl]-pyridazine (30% w/v). The self-emulsifying liquid thus obtained may be diluted with water and applied at a rate of 1 kg. of pyridazine derivative in 200 liters of spray fluid per hectare to a crop-giving area planted with soybean to control the germination and growth of *Digitaria sanguinalis, Echinochloa crus-galli, Eleusine indica, Setaria* spp. and *Amaranthus* spp. by application to the soil after sowing the crop but before crop and weeds emerge.

Similar self-emulsifying concentrates may be obtained by replacing the 3-[1-(2-ethylphenyl)ethyl]-pyridazine by a compound of general formula I wherein $R^1$ represents a fluorine, chlorine, bromine or iodine atom or a methyl, ethyl, methoxy or ethoxy group, $R^2$ represents a methyl group, $R^3$ and $R^4$ each represent a hydrogen atom and $n$ represents zero or an integer from 1 to 5 inclusive.

EXAMPLE 21

A self-emulsifying concentrate is formed by the procedure described in Example 13 but replacing the 3-(2-bromobenzyl)pyridazine by 3-[1-(2-methoxyphenyl)ethyl]pyridazine (30% w/v). The self-emulsifying liquid thus obtained may be diluted with water and applied at a rate of 0.5 kg. of pyridazine derivative in 200 liters of spray fluid per hectare to a crop-growing area sown with cotton to control the germination and growth of *Digitaria sanguinalis, Echinochloa crus-galli, Eleusine indica, Paspalum dilatatum, Setaria viridis* and *Amaranthus retroflexus* by application to the soil followed by light, shallow incorporation into the soil, before crop and weeds emerge.

EXAMPLE 22

Granules are formed by the procedure described in Example 14 but replacing the 3-(2-chlorobenzyl)pyridazine by 3-[1-(2-chlorophenyl)ethyl]pyridazine (5% w/w). The granules thus obtained may be applied to the soil of a crop-growing area containing an emerged crop of sugar-beet at a rate of 20 kg., i.e. 1 kg. of pyridazine derivative, per hectare, after 'singling' (thinning the crop) to control the germination and growth of late germinating *Amaranthus retroflexus, Chenopodium album, Digitaria sanguinalis* and *Echinochloa crus-galli.*

Similar granules may be obtained by replacing the 3-[1-(2-chlorophenyl)ethyl]pyridazine by a compound of general formula I wherein $R^1$ represents a fluorine, chlorine, bromine or iodine atom or a methyl, ethyl, methoxy or ethoxy group, $R^2$ represents a methyl group, $R^3$ and $R^4$ each represent a hydrogen atom, and $n$ represents zero or an integer from 1 to 5 inclusive.

EXAMPLE 23

A self-emulsifying concentrate is formed by the procedure described in Example 13 but replacing the 3-(2-bromobenzyl)pyridazine by (±) 3-(2-chloro-α-methoxybenzyl)pyridazine. The self-emulsifying liquid thus obtained may be diluted with water and applied at a rate of 2 kg. of pyridazine derivative in 200 liters of spray fluid per hectare to a crop-giving area planted with potatoes to control the germination and growth of *Avena fatua, Alopecurus myosuroides, Digitaria sanguinalis, Echinochloa crus-galli, Setaria viridis, Eleusine indica, Chenopodium album, Stellaria media, Polygonum* spp. and *Matricaria inodora* by application to the soil after planting the crop and before crop and weed emergence.

Similar self-emulsifying concentrates may be obtained by replacing the (±) 3-(2-chloro-α-methoxybenzyl)pyridazine by a compound of general formula I wherein $R^1$ represents a fluorine, chlorine, bromine or iodine atom or a methyl, ethyl, methoxy or ethoxy group, $R^2$ and $R^4$ each represent a hydrogen atom, $R^3$ represents a methoxy group, and $n$ represents zero or an integer from 1 to 5 inclusive.

EXAMPLE 24

Granules are formed by the procedure described in Example 14 but replacing the 3-(2-chlorobenzyl)pyridazine by (±) 3-(2-chloro-α-hydroxybenzyl)pyridazine. The granules thus obtained may be applied at a rate of 10 kg., i.e. 1 kg. of pyridazine derivative, per hectare to control the germination and growth of *Echinochloa crus-galli*, sedges, (e.g. *Eliocharis* spp. and *Fimbristylis* spp.) and broad leafed weeds, e.g. *Monochoria vaginalis* and *Rotala indica*, in a crop of transplanted rice by application before weed emergence or at early weed emergence after transplanting the crop.

Similar granules may be obtained by replacing the (±) 3-(2-chloro-α-hydroxybenzyl)pyridazine by a compound of general formula I wherein $R^1$ represents a fluorine, chlorine, bromine or iodine atom or a methyl, ethyl, methoxy or ethoxy group, $R^2$ and $R^4$ each represent a hydrogen atom, $R^3$ represents a hydroxy group, and $n$ represents zero or an integer from 1 to 5 inclusive.

EXAMPLE 25

A wettable powder is formed by the procedure described in Example 12 but replacing the 3-(2-methylbenzyl)pyridazine by 3-(2-chlorobenzoyl)pyridazine (50% w/w) and utilizing Ethylan CP (2.5% w/w) and Celite PF (47.5% w/w). The wettable powder thus obtained may be suspended in water and applied at a rate of 2 kg. of pyridazine derivative in 200 liters of spray fluid per hectare in a crop of cotton soon after sowing the crop to control the germination and growth of *Echinochloa crus-galli, Digitaria sanguinalis, Paspalum dilatatum, Eleusine indica, Chenopodium album, Polygonum* spp. and *Amaranthus retroflexus*, application being made to the soil before emergence of crop and weeds and the formulation being incorporated into the soil by overhead irrigation.

Similar wettable powders may be obtained by replacing the 3-(2-chlorobenzoyl)pyridazine by a compound of general formula I wherein $R^1$ represents a fluorine, chlorine, bromine or iodine atom or a methyl, ethyl, methoxy or ethoxy group, $R^2$ and $R^3$ together represent an oxygen atom, $R^4$ represents a hydrogen atom, and $n$ represents zero or an integer from 1 to 5 inclusive.

EXAMPLE 26

A water-soluble concentrate is formed by the procedure described in Example 16 but replacing the 3-(2-methoxybenzyl) pyridazine by 3-(2-methyl-α-hydroxyiminobenzyl)pyridazine (25% w/v). The water-soluble concentrate thus obtained may be dissolved in water and applied at a rate of 2 kg. of pyridazine derivative in 300 liters of spray fluid per hectare to a crop-growing area to be planted with cabbage to control the germination and growth of *Avena fatua, Alopecurus myosuroides, Poa annua, Stellaria media, Polygonum* spp. and *Capsella* bursa-pastoris by application to the soil followed by light, shallow mechanical incorporation, before sowing the crop.

Similar water-soluble concentrates may be obtained by replacing the 3-(2-methyl-α-hydroxyiminobenzyl)-pyridazine by a compound of a general formula I wherein $R^1$ respresents a fluorine, chlorine, bromine or iodine atom or a methyl, ethyl, methoxy or ethoxy group, $R^2$ and $R^3$ together represent the hydroxyimino group, $R^4$ represents a hydrogen atom, and $n$ represents zero or an integer from 1 to 5 inclusive.

We claim:

1. pyridazine of the formula:

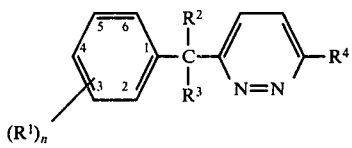

wherein $R^1$ represents fluorine. chlorine, bromine or iodine, or an alkyl, alkoxy, alkylthio, alkylsulphonyl, nitro, trifluoromethyl, cyano, monoalkylamino or dialkylamino group, the said alkyl group and the alkyl moieties of said alkoxy, alkylthio, alkylsulphonyl, monoalkylamino and dialkylamino groups having from 1 to 6 carbon atoms, $R^2$ represents hydrogen or an alkyl group of 1 to 6 carbon atoms, $R^3$ represents hydrogen, fluorine, chlorine or bromine, or an alkyl group of 1 to 6 carbon atoms, or a methoxy, ethoxy or hydroxy group, $R^4$ represents hydrogen or an alkyl group of 1 to 6 carbon atoms, and $n$ represents zero or an integer from 1 to 3 inclusive, the $R^1$ radicals being the same or different when $n$ is greater than 1, and agriculturally-acceptable salts thereof.

2. A pyridazine derivative according to claim 1 wherein $R^1$ represent fluorine, chlorine, or bromide, or an alkyl, alkoxy, or alkylthio group, the said alkyl group and the alkyl moieties of said alkoxy and alkylthio groups having from 1 to 6 carbon atoms.

3. A pyridazine according to claim 2 wherein $R^1$ represents fluorine, chlorine, or bromine, or a methyl, ethyl, methoxy or ethoxy group, $R^2$ and $R^3$ each represent hydrogen, or $R^2$ represents a methyl or ethyl group and $R^3$ represents hydrogen, or $R^2$ represents hydrogen and $R^3$ represents a methoxy, ethoxy or hydroxy group, $R^4$ represents hydrogen, and $n$ represents zero or an integer from 1 to 3 inclusive.

4. A pyridazine according to claim 3 wherein $n$ represents zero, 1, or 2.

5. A pyridazine according to claim 3 wherein $n$ represents 1 or 2 and the substituent(s) represented by the symbol $R^1$ is in the 2-position, or are in the 2,3- or 2,4-positions, of the phenyl group.

6. A pyridazine according to claim 2 wherein $R^1$ represents fluorine, chlorine or bromine, or a methyl, ethyl or methoxy group, $R^2$ represents hydrogen and $R^3$ represents a hydroxy group, $R^4$ represents hydrogen, $n$ represents 1 or 2 and the substituent(s) represented by the symbol $R^1$ is in the 2-position, or are in the 2,3- or 2,4-positions, of the phenyl group.

7. A pyridazine according to claim 6 wherein $n$ represents 1 and the symbol $R^1$ represents chlorine in the 2-position of the phenyl group.

8. A pyridazine according to claim 2 wherein $R^1$ represents fluorine, chlorine or bromine, or a methyl, ethyl or methoxy group, $R^2$ represents hydrogen, $R^3$ represents an ethyl group, $R^4$ represents hydrogen, and $n$ represents 1 or 2 and the substituent(s) represented by the symbol $R^1$ is in the 2-position, or are in the 2,3- or 2,4-positions, of the phenyl group.

9. A pyridazine according to claim 2 wherein $R^1$ represents fluorine, chlorine or bormine, or a methyl, ethyl or methoxy group, $R^2$ and $R^3$ each represent hydrogen or $R^2$ represents hydrogen and $R^3$ represents a methyl or methoxy group, $R^4$ represents hydrogen, and $n$ represents zero, 1 or 2.

10. A pyridazine according to claim 9 wherein $n$ represents 1 or 2 and the substituent(s) represented by the symbol $R^1$ is in the 2-position, or are in the 2,3- or 2,4-positions, of the phenyl group.

11. The pyridazine derivative according to claim 1 which is 3-(2-chloro-α-hydroxybenzyl)pyridazine.

12. A pyridazine according to claim 1 wherein $R^2$ represents hydrogen or an alkyl group of 1 to 6 carbon atoms and $R^3$ represents hydrogen, fluorine, chlorine or bromine, or an alkyl group of 1 to 6 carbon atoms or a hydroxy group, and $R^1$, $R^4$ and $n$ are as defined in claim 1.

13. The pyridazine derivative according to claim 1 which is 3-[1-(3-chlorophenyl)ethyl]pyridazine.

14. The pyridazine derivative according to claim 1 which is 3-[1-(2-methylphenyl)propyl]pyridazine.

15. The pyridazine derivative according to claim 1 which is 3-(2-methylbenzyl)pyridazine.

16. The pyridazine derivative according to claim 1 which is 3-(2-methoxybenzyl)pyridazine.

17. The pyridazine derivative according to claim 1 which is 3-(2-chlorobenzyl)pyridazine.

18. The pyridazine derivative according to claim 1 which is 3-(2-fluorobenzyl)pyridazine.

19. The pyridazine derivative according to claim 1 which is 3-(2-bromobenzyl)pyridazine.

20. The pyridazine derivative according to claim 1 which is 3-(2-ethylbenzyl)pyridazine.

21. The pyridazine derivative according to claim 1 which is 3-(2,4-dimethylbenzyl)pyridazine.

22. The pyridazine derivative according to claim 1 which is 3-(2,3-dimethylbenzyl)pyridazine.

23. The pyridazine derivative according to claim 1 which is 3-(1-phenylethyl)pyridazine.

24. The pyridazine derivative according to claim 1 which is 3-[1-(2-methylphenyl)ethyl]pyridazine.

25. The pyridazine derivative according to claim 1 which is 3-[1-(2-chlorophenyl)ethyl]pyridazine.

26. The pyridazine derivative according to claim 1 which is 3-[1-(2-fluorophenyl)ethyl]pyridazine.

27. The pyridazine derivative according to claim 1 which is 3-[1-(2-bromophenyl)ethyl]pyridazine.

28. The pyridazine derivative according to claim 1 which is 3-[1-(2-methoxyphenyl)ethyl]pyridazine.

29. The pyridazine derivative according to claim 1 which is 3-[1-(2-ethylphenyl)ethyl]pyridazine.

30. The pyridazine derivative according to claim 1 which is 3-[1-(2,4-dimethylphenyl)ethyl]pyridazine.

31. The pyridazine derivative according to claim 1 which is 3-[1-(4-chloro-2-methylphenyl)ethyl]pyridazine.

32. The pyridazine derivative according to claim 1 which is 3-[1-(2,3-dichlorophenyl)ethyl]pyridazine.

33. The pyridazine derivative according to claim 1 which is 3-(2-methyl-α-methoxybenzyl)pyridazine.

34. The pyridazine derivative according to claim 1 which is 3-(α,2-dimethoxybenzyl)pyridazine.

35. The pyridazine derivative according to claim 1 which is 3-(2-chloro-α-methoxybenzyl)pyridazine.

36. The pyridazine derivative according to claim 1 which is 3-(2-bromo-α-methoxybenzyl)pyridazine.

37. The pyridazine derivative according to claim 1 which is 3-(2-ethyl-α-methoxybenzyl)pyridazine.

38. A herbicidal composition which comprises a pyridazine as claimed in claim 1, or an agriculturally-acceptable salt thereof, in association with one or more compatible herbicidally-acceptable diluents or carriers, the amount of pyridazine compound in the composition being 0.05 to 90% by weight of the composition.

39. A pre-emergent or post-emergent method of controlling the growth of weeds at a locus which comprises applying to the locus a herbicidasl composition containing a herbicidally-effective amount of a pyridazine compound as claimed in claim 1.

40. A method according to claim 39, in which the herbicidal composition is applied in a directional manner in an orchard, plantation, or shrubbery, so that the composition is applied preferentially to the soil in which weeds are expected to appear.

41. A method according to claim 39, in which the pyridazine compound is applied to the locus at a rate between ¼ and 8 kg. per hectare.

42. A method according to claim 39 in which weeds controlled by application of the herbicidal composition are one or more of *Avena* spp., *Alopecurus* spp. *Setaria* spp., *Echinochloa* spp., Eleusine spp., *Bromus* spp., *Digitaria* spp., *Lolium* spp., *Poa* spp., *Paspalum* spp., *Apera spica-venti, Sorghum halepense, Agropyron repens, Agrostic* spp., *Holcus mollis, Chenopodium* spp., *Amaranthus* spp., *Polygonum* spp., *Stellaria* spp., *Gallium* spp., *Lamium* spp., *Matricaria* spp., *Portulaca* spp., *Papaver rhoeas, Capsella bursa-pastoris, Sinapis* spp., *Thlaspi arvense* and *Veronica* spp.

43. A method according to claim 39 in which weeds controlled by application of the herbicidal composition are one or more of *Monochoria vaginalis, Rotala indica, Cyperus* spp., *Eliocharis* spp. and *Fimbristylis* spp.

44. A method according to claim 39 in which the herbicidal composition is applied to a crop-growing area at a rate sufficient to control the growth of weeds without causing substantial permanent damage to the crop.

45. A method according to claim 44 in which the crop is beans, cotton, peas, flax, sugar-beet, tomatoes, groundnuts, sun flowers, Brassicas, potatoes, or a cereal crop.

46. A method according to claim 45 in which the crop is of soya beans, dwarf beans, tic beans, oilseed rape, cabbage, broccoli, Brussels sprouts, barley, wheat, sorghum, maize, rye, or rice.

47. A method according to claim 40 in which the composition is applied in a rubber, oil palm or sugar cane plantation, or in an area used for growing black currants or red currants.

* * * * *